United States Patent [19]
Uknes et al.

[11] Patent Number: 5,986,082
[45] Date of Patent: Nov. 16, 1999

[54] ALTERED FORMS OF THE NIM1 GENE CONFERRING DISEASE RESISTANCE IN PLANTS

[75] Inventors: Scott Joseph Uknes, Apex; Michelle Denise Hunt, Chapel Hill; Henry-York Steiner, Apex; John Andrew Ryals, Cary, all of N.C.

[73] Assignee: Novartis AG, Basel, Switzerland

[21] Appl. No.: 08/989,478

[22] Filed: Dec. 12, 1997

Related U.S. Application Data

[60] Provisional application No. 60/033,177, Dec. 13, 1996, provisional application No. 60/034,379, Dec. 27, 1996, provisional application No. 60/034,382, Dec. 27, 1996, provisional application No. 60/034,730, Jan. 10, 1997, provisional application No. 60/035,021, Jan. 10, 1997, and provisional application No. 60/035,022, Jan. 10, 1997.

[51] Int. Cl.$^6$ .............................. C12N 5/04; C12N 15/29; A01H 4/00; A01H 5/00
[52] U.S. Cl. ........................ 536/23.6; 800/278; 800/205; 800/279
[58] Field of Search .......................... 536/23.6; 800/205, 800/DIG. 17, 278, 279

[56] References Cited

U.S. PATENT DOCUMENTS 5,614,395  3/1997  Ryals et al. .

FOREIGN PATENT DOCUMENTS

| 0 534 858 | 3/1993 | European Pat. Off. . |
|---|---|---|
| WO 94/16077 | 7/1994 | WIPO . |
| WO 95/19443 | 7/1995 | WIPO . |

OTHER PUBLICATIONS

Genbank Accession No. T22612, Cao et al., Cell 88(1): 57–63 (1997).
Genbank Accession No. U76707, Newman et al., Plant Physiol., 106: 1241–1255 (1994).
Dong et al., U.S. Provisional Application No. 60/023,851, filed Aug. 9, 1996.
Dong et al., U.S. Provisional Application No. 60/035,166, filed Jan. 10, 1997.
Roche et al. Plant Molecular Biology. 1993. vol. 22: 971–983.
Napoli et al. The Plant Cell. 1989. vol.2: 278–289.
Linthorst et al. The Plant Cell. 1989. vol. 1: 285–291.
Valvekens et al. Proc. Natl. Acad.Sci. 1988. vol. 85: 5536–5540.
Coleman et al. Cell. 1993. Mar. issue. vol. 72: 919–929.
Martin et al. Science. 1993. Nov. issue. vol. 262: 1432–1436.
Alexander et al., "Increased tolerance to two oomycete pathogens in transgenic tobacco expressing pathogenesis–related protein 1a", *Proc. Natl. acad. Sci.* 90: 7327–7331 (1993).
Baeuerle and Baltimore, "NF–κB: Ten Years After", *Cell*, 87: 13–20 (1996).
Baldwin, A.S., "The NF–κB and IκB Proteins: New Discoveries and Insights", *Annu. Rev. Immunol.*, 14: 649–681 (1996).
Beg and Baltimore, "An Essential Role for NF–κB in Preventing TNF–α–Induced Cell Death", *Science*, 274: 782–784 (1996).
Bell et al., "Assignment of 30 Microsatellite Loci to the Linkage Map of Arabidopsis", *Genomics* 19, 137–144 (1994).
Bhat, K.S., "Generation of a plasmid vector for deletion cloning by rapid multiple site–directed mutagenesis", *Gene* 134: 83–87 (1993).
Bi et al., "Hydrogen peroxide does not function downstream of salicylic acid in the induction of PR protein expression", *The Plant Journal*, 8(2): 235–245 (1995).
Bouchez et al., "A new YAC library for genome mapping in Arabidopsis", Abstract, 6th International Conference on Arabidopsis Research (1995).
Bowling et al., "A Mutation in Arabidopsis That Leads to Constitutive Expression of Systemic Acquired Resistance", *The Plant Cell*, 6: 1845–1857 (1994).
Bowling et al., "The cpr5 Mutant of Arabidopsis Expresses Both NPR1–Dependent and NPR1–Independent Resistance", *The Plant Cell*, 9: 1573–1584 (1997).
Brockman et al., "Coupling of a Signal Response Domain in IκBα to Multiple Pathways for NF–κB Activation", *Molecular and Cellular Biology*, 15: 2809–2818 (1995).
Brown et al., "Control of IκB–α Proteolysis by Site–Specific, Signal–Induced Phosphorylation", *Science*, 267: 1485–1488 (1995).
Büschges et al., "The Barley Mlo Gene: A Novel Control Element of Plant Pathogen Resistance", *Cell*, 88: 695–704 (1997).
Cameron et al., "Biologically induced systemic acquired resistance in *Arabidopsis thaliana*", *The Plant Journal* 5(5): 715–725 (1994).

(List continued on next page.)

*Primary Examiner*—Gary Benzion
*Assistant Examiner*—Ousama M-Faiz Zaghmout
*Attorney, Agent, or Firm*—J. Timothy Meigs

[57] ABSTRACT

The NIM1 gene product is a structural homologue of the mammalian signal transduction factor IκB subclass α. The present invention exploits this discovery to provide altered forms of NIM1 that act as dominant-negative regulators of the systemic acquired resistance (SAR) signal transduction pathway. These altered forms of NIM1 confer the opposite phenotype as the nim1 mutant in plants transformed with the altered forms of NIM1; i.e., the transgenic plants exhibit constitutive SAR gene expression and a constitutive immunity (CIM) phenotype. The present invention further concerns DNA molecules encoding altered forms of the NIM1 gene, expression vectors containing such DNA molecules, and plants and plant cells transformed therewith. The invention also concerns methods of activating SAR in plants and conferring to plants a CIM phenotype and broad spectrum disease resistance by transforming the plants with DNA molecules encoding altered forms of the NIM1 gene product.

10 Claims, 3 Drawing Sheets

OTHER PUBLICATIONS

Cao et al., "Characterization of an Arabidopsis Mutant That Is Nonresponsive to Inducers of Systemic Acquired Resistance", *The Plant Cell*, 6: 1583–1592 (1994).

Cao et al., "The Arabidopsis NPR1 Gene that Controls Systemic Acquired Resistance Encodes a Novel Protein Containing Ankyrin Repeats", *Cell*, 88: 57–63 (1997).

Century et al., "NDR1, a locus of *Arabidopsis thaliana* that is required for disease resistance to both a bacterial and a fungal protein", *Proc. Natl. Acad. Sci.*, 92: 6597–6601 (1995).

Creusot et al., "The CIC library: a large insert YAC library for genome mapping in *Arabidopsis thaliana*", *The Plant Journal*, 8(5): 763–770 (1995).

Dangl et al., "Death Don't Have No Mercy: Cell Death Programs in Plant–Microbe Interactions", *The Plant Cell*, 8: 1793–1807 (1996).

Delaney et al., "A Central Role of Salicylic Acid in Plant Disease Resistance", *Science*, 266: 1247–1250 (1994).

Delaney et al., "Arabidopsis signal transduction mutants defective in chemically and biologically induced disease resistance", Abstract, 6th International Meeting on Arabidopsis Research, (1995).

Delaney et al., "Arabidopsis signal transduction mutant defective in chemically and biologically induced disease resistance", *Proc. Natl. Acad. Sci.*, 92: 6602–6606 (1995).

Delaney, T.P., "Genetic Dissection of Acquired Resistance to Disease", *Plant Physiol.* 113: 1–12 (1997).

de Martin et al., "Cytokine–inducible expression in endothelial cells of an IκBα–like gene is regulated by NFκB", *EMBO J.* 12: 2773–2779 (1993).

de Martin et al., "Intron–exon structure of the porcine IκBα–encoding gene . . . ", *Gene*, 152: 253–255 (1995).

Dietrich et al., "Arabidopsis Mutants Simulating Disease Resistance Response", *Cell* 77: 565–577 (1994).

Elledge et al., "λYes: Amultifunctional cDNA expression vector for the isolation of genes by complementation of yeast and *Escherichia coli* mutations", *Proc. Natl. Acad. Sci., USA* 88:1731–1735 (1991).

Friedrich et al., "A benzothiadiazole derivative induces systemic acquired resistance in tobacco", *The Plant Journal*, 10: 61–70 (1996).

Gaffney et al., "Requirement of Salicylic Acid for the Induction of Systemic Acquired Resistance", *Science* 261: 754–756 (1993).

Gatz C., "Chemical Control of Gene Expression", *Ann. Rev. Plant Physiol. Plant Mol. Biol.* 48: 89–108 (1997).

Glazebrook et al., "Isolation of Arabidopsis Mutants With Enhanced Disease Susceptibility by Direct Screening", *Genetics* 143: 973–982 (1996).

Görlach et al., "Benzothiadiazole, a Novel Class of Inducers of Systemic Acquired Resistance, Activates Gene Expression and Disease Resistance in Wheat", *The Plant Cell* 8: 629–643 (1996).

Greenberg et al., "Programmed Cell Death in Plants: A Pathogen–Triggered Response Activated Coordinately with Multiple Defense Functions", *Cell* 77: 551–563 (1994).

Hebsgaard et al., "Splice site prediction in *Arabidopsis thaliana* pre–mRNA by combining local and global sequence information", *Nucleic Acids Research* 24: 3439–3452 (1996).

Hunt et al., "Systemic Acquired Resistance Signal Transduction", *Critical Reviews in Plant Sciences* 15: 583–606 (1996).

Ip et al., "Dif, a dorsal–Related Gene That Mediates an Immune Response in Drosophila", *Cell*, 75: 753–763 (1993).

Kessmann et al., "Induction of Systemic Acquired Disease Resistance in Plants by Chemicals", *Annu. Rev. Phytopathol.* 32: 439–459 (1994).

Kopp and Ghosh, "Inhibition of NF–κB by Sodium Salicylate and Aspirin", *Science*, 265: 956–959 (1994).

Lawton et al., "The Molecular Biology of Systemic Acquired Resistance", *Mechanisms of Plant Defense Responses*, B. Fritig and M. Legrand (eds.) Kluwer Academic Publishers (Netherlands) 422–432 (1993).

Lawton et al., "Systemic Acquired Resistance in Arabidopsis Requires Salicylic Acid but Not Ethylene", *Molecular Plant–Microbe Interactions* 8: 863–870 (1995).

Lawton et al., "Benzothiadiazole induces disease resistance in Arabidopsis by activation of the systemic acquired resistance signal transduction pathway" *The Plant Journal* 10: 71–82 (1996).

Lemaitre et al., "The Dorsoventral Regulatory Gene Cassette spätzle/Toll/cactus Controls the Potent Antifungal Response in Drosophila Adults", *Cell*, 86: 973–983 (1996).

Lister et al., "Recombinant inbred lines for mapping RFLP and phenotypic markers in *Arabidopsis thaliana*" *The Plant Journal* 4: 745–750 (1993).

Liu et al., "Generation of high–quality P1 library of Arabidopsis suitable for chromosome walking", *The Plant Journal* 7: 351–358 (1995).

Maher et al., "Increased disease susceptibility of transgenic tobacco plants with suppressed levels of preformed phenylpropanoid products", *Proc. Natl. Acad. Sci., USA*, 91: 7802–7806 (1994).

Mauch–Mani et al., "Systemic Acquired Resistance in *Arabidopsis thaliana* Induced by a Predisposing Infection with a Pathogenic Isolate of *Fusarium oxysporum*", *Molecular Plant–Microbe Interactions* 7: 378–383 (1994).

Mauch–Mani et al., "Production of Salicylic Acid Precursors Is a Major Function of Phenylalanine Ammonia–Lyase in the Resistance of Arabidopsis to *Peronospora parasitica*", *The Plant Cell* 8: 203–212 (1996).

Métraux et al., "Increase in Salicylic Acid at the Onset of Systemic Acquired Resistance in Cucumber", *Science* 250: 1004–1006 (1990).

Michaely and Bennett, "The ANK repeat: a ubiquitous motif involved in macromolecular recognition", *Trends in Cell Biology* 2: 127–129 (1992).

Mindrinos et al., "The *A. thaliana* Disease Resistance Gene RPS2 Encodes a Protein Containing a Nucleotide–Binding Site and Leucine–Rich Repeats", *Cell* 78: 1089–1099 (1994).

Pallas et al., "Tobacco plants epigenetically suppressed in phenylalanine ammonia–lyase expression do not develop systemic acquired resistance in response to infection by tobacco mosaic virus", *The Plant Journal* 10: 281–293 (1996).

Parker et al., "Characterization of eds1, a Mutation in Arabidopsis Suppressing Resistance to *Peronospora parasitica* Specified by Several Different RPP Genes", *The Plant Cell* 8: 2033–2046 (1996).

Payne et al., "Isolation of the genomic clone for pathogenesis–related protein 1a from *Nicotiana tabacum* cv. Xanthi–nc", *Plant Molecular Biology* 11: 89–94 (1988).

Ryals et al., "Signal transduction in systemic acquired resistance", *Proc. Natl. Acad. Sci. USA* 92: 4202–4205 (1995).

Ryals et al., "Systemic Acquired Resistance", *The Plant Cell* 8: 1809–1819 (1996).

Ryals et al., "The Arabidopsis NIM1 Protein Shows Homology to the Mammalian Transcription Factor Inhibitor IkB", *The Plant Cell* 9: 425–439 (1997).

Service, R.F., "Closing In on a Stomach–Sparing Aspirin Substitute", *Science*, 273: 1660 (1996).

Shulaev, et al., "Is Salicylic Acid a Translocated Signal of Systemic Acquired Resistance in Tobacco?", *The Plant Cell* 7: 1691–1701 (1995).

Simoens et al., "Isolation of genes expressed in specific tissues of *Arabidopsis thaliana* by differential screening of a genomic library", *Gene* 67: 1–11 (1988).

Sun et al., "Both Amino– and Carboxyl–Terminal Sequences within IκBα Regulate Its Inducible Degradation", *Molecular and Cellular Biology*, 16: 1058–1065 (1996).

Tewari et al., "Sequence of rat RL/IF–1 encoding IKBβ–like activity and comparison with related proteins containing notch–like repeats", *Nucleic Acids Research*, 20: 607 (1992).

Traenckner, E.Britta–Mareen, "Phosphorylation of human IκB–α of serines 32 and 36 controls IκB–α proteolysis and NF–κB activation in response to diverse stimuli", *EMBO Journal*, 14: 2876–2883 (1995).

Uknes et al., "Acquired Resistance in Arabidopsis", *The Plant Cell* 4: 645–656 (1992).

Uknes et al., "Regulation of Pathogenesis–Related Protein–1a Gene Expression in Tobacco", *The Plant Cell* 5: 159–169 (1993).

Uknes et al., "Biological Induction of Systemic Acquired Resistance in Arabidopsis", *Molecular Plant–Microbe Interactions* 6: 692–698 (1993).

Uknes et al., "Reduction of risk for growers: methods for the development of disease–resistant crops", *New Phytol.* 133: 3–10 (1996).

Van Antwerp et al., "Suppression of TNF–α–Induced Apoptosis by NF–κB", *Science*, 274: 787–789 (1996).

Vernooij et al., "Salicylic Acid Is Not the Translocated Signal Responsible for Inducing Systemic Acquired Resistance but Is Required in Signal Transduction", *The Plant Cell* 6: 959–965 (1994).

Vernooij et al., "2,6–Dichloroisonicotinic Acid–Induced Resistance to Pathogens Without the Accumulation of Salicylic Acid", *Molecular Plant–Microbe Interactions* 8: 228–234 (1995).

Verwoerd et al., "A small–scale procedure for the rapid isolation of plant RNAs", *Nucleic Acids Research* 17: 2362 (1989).

Vos et al., "AFLP: a new technique for DNA fingerprinting", *Nucleic Acids Research* 23: 4407–4414 (1995).

Wang et al., "TNF– and Cancer Therapy–Induced Apoptosis: Potentiation by Inhibition of NF–κB", *Science*, 274: 784–787 (1996).

Ward et al., "Coordinate Gene Activity in Response to Agents That Induce Systemic Acquired Resistance", *The Plant Cell* 3: 1085–1094 (1991).

Weymann et al., "Suppression and Restoration of Lesion Formation in Arabidopsis Isd Mutants", *The Plant Cell* 7: 2013–2022 (1995).

GenBank Accession No. T22612.

GenBank Accession No. U76707.

FIGURE 1A

```
            301                +                 +                 +               350                +                 +                 +               400
NIM1            CALHPAVAYCNVKIATDLLKLDLADVNHRNP.RGYTVLHVAAMRKEEQLILSLLEK.GASASEATLEGRTALMIAKQAITMAVECNNIPEQCKHSLKGRLC    394
MOUSE I-κBα     C.LHLASIHGYLAIVEHLVTLG.ADVNAQEPCNGRTALHLAVDLQNPDLV.SLLLKCGADVNRVTYQG...........................           250
RAT I-κBα       C.LHLASIHGYLGIVEHLVTLG.ADVNAQEPCNGRTALHLAVDLQNPDLV.SLLLKCGADVNRVTYQG...........................           250
PIG I-κBα       C.LHLASIHGYLGIVEHLVSLG.ADVNAQEPCNGRTALHLAVDLQNPDLV.SLLLKCGADVNRVTYQG...........................           250

401                +                 +                 +               450                +                 +                 +               500
NIM1            VEILEQEDKREQIPRDVPPSFAVAADELKMTLIDLENRVALAQRLFPTEAQAAMELAEMKGICEFIVISLEPDRLIGIKRTSPGVKIAPFRILEEHQSRL           494
MOUSE I-κBα     ............................................................YSPYQLT..WGRPSTRIQQ................           267
RAT I-κBα       ............................................................YSPYQLT..WGRPSTRIQQ................           267
PIG I-κBα       ............................................................YSPYQLT..WGRPSTRIQQ................           267

501                +                 +                 +               550                +                 +                 +               600
NIM1            KALSKTVELGKRFFPRCSAVLDQIMNEDLITQLACGEDDITAEKRLQKKQRYMEIQETLKKAFSEDNLELGNSSLIDSTSSTSKSTGEKRSNRKLSHRRR           593
MOUSE I-κBα     ...QLGQ...........LITLENLQMLPESEDE..........ESYDIESE.....FTEDELPYDDCVF..................GGQR....LTL.           314
RAT I-κBα       ...QLGQ...........LITLENLQTLPESEDE..........ESYDIESE.....FTEDELPYDDCVF..................GGQR....LTL.           314
PIG I-κBα       ...QLGQ...........LITLENLQMLPESEDE..........ESYDIESE.....FTEDELPYDDCVL..................GGQR....LTL.           314
```

FIGURE 1B

| | | |
|---|---|---|
| NIM1 | : | 267 VSNVHKALDSDDIELVKLLLKEDHTNLDDACALHFAVAYCN 307 |
| | |     +   +  +ALD+ DIELVKL++    +    +LDDA A+H+AV +CN |
| Rice-1 | : | 33 IRRMRRALDAADIELVKLMVGEGLDLDDALAVHYAVQHCN 155 |
| NIM1 | : | 327 PRGYTVLHVAAMRKEPQLILSLLEKGASASEATLEGRT 364 |
| | |     P G T LH+AA     P ++   LL+   A  +   T +G T |
| Rice-1 | : | 215 PTGKTALHLAAEMVSPDMVSVLLDHHADXNFRTXDGVT 328 |
| | | |
| NIM1 | : | 267 VSNVHKALDSDDIELVKLLLKEDHTNLDDACALHFAVAYCN 307 |
| | |     +   +  +ALD+ DIELVKL++    +    +LDDA A+H+AV +CN |
| Rice-2 | : | 33 IRRMRRALDAADIELVKLMVGEGLDLDDALAVHYAVQHCN 155 |
| NIM1 | : | 325 RNPRGYTVLHVAAMRKEPQLILSLLEK 351 |
| | |     R P    T LH+AA     P ++   LL++ |
| Rice-2 | : | 208 RRPDSKTALHLAAEMVSPDMVSVLLDQ 288 |
| | | |
| NIM1 | : | 267 VSNVHKALDSDDIELVKLLLKEDHTNLDDACALHFAVAYCN 307 |
| | |     +   +  +ALD+ DIELVKL++    +    +LDDA A+H+AV +CN |
| Rice-3 | : | 33 IRRMRRALDAADIELVKLMVGEGLDLDDALAVHYAVQHCN 155 |
| NIM1 | : | 325 RNPRGYTVLHVAAMRKEPQLILSLLEK 351 |
| | |     R P    T LH+AA     P ++   LL++ |
| Rice-3 | : | 208 RRPDSKTALHLAAEMVSPDMVSVLLDQ 288 |
| | | |
| NIM1 | : | 267 VSNVHKALDSDDIELVKLLLKEDHTNLDDACALHFAVAYCN 307 |
| | |     +   +  +ALD+ DIELVKL++    +    +LDDA A+H+AV +CN |
| Rice-4 | : | 33 IRRMRRALDAADIELVKLMVGEGLDLDDALAVHYAVQHCN 155 |
| NIM1 | : | 327 PRGYTVLHVAAMRKEPQLI 345 |
| | |     P G T LH+AA     P ++ |
| Rice-4 | : | 215 PTGKTALHLAAEMVSPDMV 271 |

FIGURE 2

ALTERED FORMS OF THE NIM1 GENE CONFERRING DISEASE RESISTANCE IN PLANTS

This application claims the benefit of U.S. Provisional Application No. 60/033,177, filed Dec. 13, 1996; U.S. Provisional Application No. 60/034,379, filed Dec. 27, 1996; U.S. Provisional Application No. 60/034,382, filed Dec. 27, 1996; U.S. Provisional Application No. 60/034,730, filed Jan. 10, 1997; U.S. Provisional Application No. 60/035,021, filed Jan. 10, 1997; and U.S. Provisional Application No. 60/035,022, filed Jan. 10, 1997. The disclosures of each of these U.S. Provisional Applications are hereby expressly incorporated by reference in their entireties into the instant disclosure.

FIELD OF THE INVENTION

The present invention generally relates to broad-spectrum disease resistance in plants, including the phenomenon of systemic acquired resistance (SAR). More particularly, the present invention relates to the recombinant expression of altered forms of the NIM1 gene, which is involved in the signal transduction cascade leading to SAR, to create transgenic plants having broad-spectrum disease resistance.

BACKGROUND OF THE INVENTION

Systemic Acquired Resistance (SAR)

Plants are constantly challenged by a wide variety of pathogenic organisms including viruses, bacteria, fungi, and nematodes. Crop plants are particularly vulnerable because they are usually grown as genetically-uniform monocultures; when disease strikes, losses can be severe. However, most plants have their own innate mechanisms of defense against pathogenic organisms. Natural variation for resistance to plant pathogens has been identified by plant breeders and pathologists and bred into many crop plants. These natural disease resistance genes often provide high levels of resistance to or immunity against pathogens.

Systemic acquired resistance (SAR) is one component of the complex system plants use to defend themselves from pathogens (Hunt and Ryals, *Crit. Rev. in Plant Sci.* 15, 583–606 (1996), incorporated by reference herein in its entirety; Ryals et al., *Plant Cell* 8, 1809–1819 (1996), incorporated by reference herein in its entirety). See also, U.S. Pat. No. 5,614,395, incorporated by reference herein in its entirety. SAR is a particularly important aspect of plant-pathogen responses because it is a pathogen-inducible, systemic resistance against a broad spectrum of infectious agents, including viruses, bacteria, and fungi. When the SAR signal transduction pathway is blocked, plants become more susceptible to pathogens that normally cause disease, and they also become susceptible to some infectious agents that would not normally cause disease (Gaffney et al., *Science* 261, 754–756 (1993), incorporated by reference herein in its entirety; Delaney et al., *Science* 266, 1247–1250 (1994), incorporated by reference herein in its entirety; Delaney et al., *Proc. Natl. Acad. Sci. USA* 92, 6602–6606 (1995), incorporated by reference herein in its entirety; Delaney, *Plant Phys.* 113, 5–12 (1997), incorporated by reference herein in its entirety; Bi et al., *Plant J.* 8, 235–245 (1995), incorporated by reference herein in its entirety; Mauch-Mani and Slusarenko, *Plant Cell* 8, 203–212 (1996), incorporated by reference herein in its entirety). These observations indicate that the SAR signal transduction pathway is critical for maintaining plant health.

Conceptually, the SAR response can be divided into two phases. In the initiation phase, a pathogen infection is recognized, and a signal is released that travels through the phloem to distant tissues. This systemic signal is perceived by target cells, which react by expression of both SAR genes and disease resistance. The maintenance phase of SAR refers to the period of time, from weeks up to the entire life of the plant, during which the plant is in a quasi steady state, and disease resistance is maintained (Ryals et al., 1996).

Salicylic acid (SA) accumulation appears to be required for SAR signal transduction. Plants that cannot accumulate SA due to treatment with specific inhibitors, epigenetic repression of phenylalanine ammonia-lyase, or transgenic expression of salicylate hydroxylase, which specifically degrades SA, also cannot induce either SAR gene expression or disease resistance (Gaffney et al., 1993; Delaney et al., 1994; Mauch-Mani and Slusarenko 1996; Maher et al., *Proc. Natl. Acad. Sci. USA* 91, 7802–7806 (1994), incorporated by reference herein in its entirety; Pallas et al., *Plant J.* 10, 281–293 (1996), incorporated by reference herein in its entirety). Although it has been suggested that SA might serve as the systemic signal, this is currently controversial and, to date, all that is known for certain is that if SA cannot accumulate, then SAR signal transduction is blocked (Pallas et al., 1996; Shulaev et al., *Plant Cell* 7, 1691–1701 (1995), incorporated by reference herein in its entirety; Vernooij et al., *Plant Cell* 6, 959–965 (1994), incorporated by reference herein in its entirety).

Recently, Arabidopsis has emerged as a model system to study SAR (Uknes et al., *Plant Cell* 4, 645–656 (1992), incorporated by reference herein in its entirety; Uknes et al., *Mol. Plant-Microbe Interact.* 6, 692–698 (1993), incorporated by reference herein in its entirety; Cameron et al., *Plant J.* 5, 715–725 (1994), incorporated by reference herein in its entirety; Mauch-Mani and Slusarenko, *Mol. Plant-Microbe Interact.* 7, 378–383 (1994), incorporated by reference herein in its entirety; Dempsey and Klessig, *Bulletin de L'Institut Pasteur* 93, 167–186 (1995), incorporated by reference herein in its entirety). It has been demonstrated that SAR can be activated in Arabidopsis by both pathogens and chemicals, such as SA, 2,6-dichloroisonicotinic acid (INA) and benzo(1,2,3)thiadiazole-7-carbothioic acid S-methyl ester (BTH) (Uknes et al., 1992; Vernooij et al., *Mol. Plant-Microbe Interact.* 8, 228–234 (1995), incorporated by reference herein in its entirety; Lawton et al., *Plant J.* 10, 71–82 (1996), incorporated by reference herein in its entirety). Following treatment with either INA or BTH or pathogen infection, at least three pathogenesis-related (PR) protein genes, namely, PR-1, PR-2, and PR-5 are coordinately induced concomitant with the onset of resistance (Uknes et al., 1992, 1993). In tobacco, the best characterized species, treatment with a pathogen or an immunization compound induces the expression of at least nine sets of genes (Ward et al., *Plant Cell* 3, 1085–1094 (1991), incorporated by reference herein in its entirety). Transgenic disease-resistant plants have been created by transforming plants with various SAR genes (U.S. Pat. No. 5,614,395).

A number of Arabidopsis mutants have been isolated that have modified SAR signal transduction (Delaney, 1997) The first of these mutants are the so-called lsd (lesions simulating disease) mutants and acd2 (accelerated cell death) (Dietrich et al., *Cell* 77, 565–577 (1994), incorporated by reference herein in its entirety; Greenberg et al., *Cell* 77, 551–563 (1994), incorporated by reference herein in its entirety). These mutants all have some degree of spontaneous necrotic lesion formation on their leaves, elevated levels of SA, mRNA accumulation for the SAR genes, and significantly enhanced disease resistance. At least seven different lsd mutants have been isolated and characterized (Dietrich et al., 1994; Weymann et al., *Plant Cell* 7, 2013–2022 (1995), incorporated by reference herein in its entirety). Another interesting class of mutants are cim (constitutive immunity) mutants (Lawton et al., "The molecular biology of systemic aquired resistance" in *Mechanisms of Defence Responses in Plants*, B. Fritig and M. Legrand, eds (Dordrecht, The Netherlands: Kluwer Academic Publishers), pp. 422–432 (1993), incorporated by reference herein in its entirety). See also, U.S. patent application Ser. No. 08/648,949 and International PCT Application WO 94/16077, both of which are incorporated by reference herein in their entireties. Like lsd mutants and acd2, cim mutants have elevated SA and SAR gene expression and resistance, but in contrast to lsd or acd2, do not display detectable lesions on their leaves. cpr1 (constitutive expresser of PR genes) may be a type of cim mutant; however, because the presence of microscopic lesions on the leaves of cpr1 has not been ruled out, cpr1 might be a type of lsd mutant (Bowling et al., *Plant Cell* 6, 1845–1857 (1994), incorporated by reference herein in its entirety).

Mutants have also been isolated that are blocked in SAR signaling. ndr1 (non-race-specific disease resistance) is a mutant that allows growth of both *Pseudomonas syringae* containing various avirulence genes and also normally avirulent isolates of *Peronospora parasitica* (Century et al., *Proc. Natl. Acad. Sci. USA* 92, 6597–6601 (1995), incorporated by reference herein in its entirety). Apparently this mutant is blocked early in SAR signaling. npr1 (nonexpresser of PR genes) is a mutant that cannot induce expression of the SAR signaling pathway following INA treatment (Cao et al., *Plant Cell* 6, 1583–1592 (1994), incorporated by reference herein in its entirety). eds (enhanced disease susceptibility) mutants have been isolated based on their ability to support bacterial infection following inoculation of a low bacterial concentration (Glazebrook et al., *Genetics* 143, 973–982 (1996), incorporated by reference herein in its entirety; Parker et al., *Plant Cell* 8, 2033–2046 (1996), incorporated by reference herein in its entirety). Certain eds mutants are phenotypically very similar to npr1, and, recently, eds5 and eds53 have been shown to be allelic to npr1 (Glazebrook et al., 1996). nim1 (noninducible immunity) is a mutant that supports *P. parasitica* (i.e., causal agent of downy mildew disease) growth following INA treatment (Delaney et al., 1995; U.S. patent application Ser. No. 08/648,949). Although nim1 can accumulate SA following pathogen infection, it cannot induce SAR gene expression or disease resistance, suggesting that the mutation blocks the pathway downstream of SA. nim1 is also impaired in its ability to respond to INA or BTH, suggesting that the block exists downstream of the action of these chemicals (Delaney et al., 1995; Lawton et al., 1996).

Recently, two allelic Arabidopsis genes have been isolated and characterized, mutants of which are responsible for the nim1 and npr1 phenotypes, respectively (Ryals et al., *Plant Cell* 9, 425–439 (1997), incorporated by reference herein in its entirety; Cao et al., *Cell* 88, 57–63 (1997), incorporated by reference herein in its entirety). The wild-type NIM1 gene product is involved in the signal transduction cascade leading to both SAR and gene-for-gene disease resistance in Arabidopsis (Ryals et al., 1997). Ryals et al., 1997 also report the isolation of five additional alleles of nim1 that show a range of phenotypes from weakly impaired in chemically induced PR-1 gene expression and fungal resistance to very strongly blocked. Transformation of the wild-type NPR1 gene into npr1 mutants not only complemented the mutations, restoring the responsiveness of SAR induction with respect to PR-gene expression and disease resistance, but also rendered the transgenic plants more resistant to infection by *P. syringae* in the absence of SAR induction (Cao et al., 1997).

NF-κB/IκB Signal Transduction Pathways

NF-κB/IκB signaling pathways have been implicated in disease resistance responses in a range of organisms from Drosophila to mammals. In mammals, NF-κB/IκB signal transduction can be induced by a number of different stimuli including exposure of cells to lipopolysaccharide, tumor necrosis factor, interleukin 1 (IL-1), or virus infection (Baeuerle and Baltimore, *Cell* 87, 13–20 (1996); Baldwin, *Annu. Rev. Immunol.* 14, 649–681 (1996)). The activated pathway leads to the synthesis of a number of factors involved in inflammation and immune responses, such as IL-2, IL-6, IL-8 and granulocyte/macrophage-colony stimulating factor (deMartin et al., *Gene* 152, 253–255 (1995)). In transgenic mouse studies, the knock-out of NF-κB/IκB signal transduction leads to a defective immune response including enhanced susceptibility to bacterial and viral pathogens (Beg and Baltimore, *Science* 274, 782–784 (1996); Van Antwerp et al., *Science* 274, 787–789 (1996); Wang et al., *Science* 274, 784–787 (1996); Baeuerle and Baltimore (1996)). In Arabidopsis, SAR is functionally analogous to inflammation in that normal resistance processes are potentiated following SAR activation leading to enhanced disease resistance (Bi et al., 1995; Cao et al., 1994; Delaney et al., 1995; Delaney et al., 1994; Gaffney et al., 1993; Mauch-Mani and Slusarenko 1996; Delaney, 1997). Furthermore, inactivation of the pathway leads to enhanced susceptibility to bacterial, viral and fungal pathogens. Interestingly, SA has been reported to block NF-κB activation in mammalian cells (Kopp and Ghosh, *Science* 265, 956–959 (1994)), while SA activates signal transduction in Arabidopsis. Bacterial infection of Drosophila activates a signal transduction cascade leading to the synthesis of a number of antifungal proteins such as cercropin B, defensin, diptericin and drosomycin (Ip et al., *Cell* 75, 753–763 (1993); Lemaitre et al., *Cell* 86, 973–983 (1996)). This induction is dependent on the gene product of dorsal and dif, two NF-κB homologs, and is repressed by cactus, an IκB homolog, in the fly. Mutants that have decreased synthesis of the antifungal and antibacterial proteins have dramatically lowered resistance to infection.

Despite much research and the use of sophisticated and intensive crop protection measures, including genetic transformation of plants, losses due to disease remain in the billions of dollars annually. Therefore, there is a continuing need to develop new crop protection measures based on the ever-increasing understanding of the genetic basis for disease resistance in plants.

SUMMARY OF THE INVENTION

The present invention exploits both the recognition that the SAR pathway in plants shows functional parallels to the NF-κB/IκB regulation scheme in mammals and flies, as well as the discovery that the NIM1 gene product is a structural homologue of the mammalian signal transduction factor IκB subclass α. Mutations of IκB have been described that act as super-repressors or dominant-negatives of the NF-κB/IκB regulation scheme. The present invention encompasses altered forms of the wild-type NIM1 gene (SEQ ID NO:1) that act as dominant-negative regulators of the SAR signal transduction pathway. These altered forms of NIM1 confer the opposite phenotype in plants transformed therewith as the nim1 mutant; i.e., plants transformed with altered forms of NIM1 exhibit constitutive SAR gene expression and a CIM phenotype.

In one embodiment of the present invention, the NIM1 gene is altered so that the encoded product has alanines instead of serines in the amino acid positions corresponding to positions 55 and 59 of the wild-type Arabidopsis NIM1 amino acid sequence (SEQ ID NO:2). An example of a preferred embodiment of this altered from of the NIM1 gene, which results in changes of these serine residues to alanine residues, is presented in SEQ ID NO:7. An exemplary dominant-negative form of the NIM1 protein with alanines instead of serines at amino acid positions 55 and 59 is shown in SEQ ID NO:8. The present invention also encompasses altered forms of alleles of NIM1, wherein the coding sequence of such an allele hybridizes under the following conditions to the coding sequence set forth in SEQ ID NO:7: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:7 under the above conditions are altered so that the encoded product has alanines instead of serines in the amino acid positions that correspond to positions 55 and 59 of SEQ ID NO:2. By "correspond to," it is meant that when the amino acid sequence of the respective allele of NIM1 is aligned with the amino acid sequence of the NIM1 gene given in SEQ ID NO:2, the amino acids in the allelic sequence that "correspond to" certain specified positions of SEQ ID NO:2 are those that align with these positions of SEQ ID NO:2, but are not necessarily in these exact positions of the allelic sequence.

In another embodiment of the present invention, the NIM1 gene is altered so that the encoded product has an N-terminal truncation, which removes lysine residues that may serve as potential ubiquitination sites in addition to the serines at amino acid positions corresponding to positions 55 and 59 of the wild-type protein. An example of a preferred embodiment of this altered form of the NIM1 gene, which encodes a gene product having an N-terminal deletion, is presented in SEQ ID NO:9. An exemplary dominant-negative form of the NIM1 protein with an N-terminal deletion is shown in SEQ ID NO:10. The present invention also encompasses altered forms of alleles of NIM1, wherein the coding sequence of such an allele hybridizes under the following conditions to the coding sequence set forth in SEQ ID NO:9: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:9 under the above conditions are altered so that the encoded product has an N-terminal deletion that removes lysine residues that may serve as potential ubiquitination sites in addition to the serines at amino acid positions corresponding to positions 55 and 59 of the wild-type gene product.

In still another embodiment of the present invention, the NIM1 gene is altered so that the encoded product has a C-terminal truncation, which is believed to result in enhanced intrinsic stability by blocking the constitutive phosporylation of serine and threonine residues in the C-terminus of the wild-type gene product. An example of a preferred embodiment of this altered form of the NIM1 gene, which encodes a gene product having a C-terminal deletion, is presented in SEQ ID NO:11. An exemplary dominant-negative form of the NIM1 protein with a C-terminal deletion is shown in SEQ ID NO:12. The present invention also encompasses altered forms of alleles of NIM1, wherein the coding sequence of such an allele hybridizes under the following conditions to the coding sequence set forth in SEQ ID NO:11: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:11 under the above conditions are altered so that the encoded product has a C-terminal deletion that removes serine and threonine residues.

In yet another embodiment of the present invention, the NIM1 gene is altered so that the encoded product has both an N-terminal deletion and a C-terminal truncation, which provides the benefits of both the above-described embodiments of the invention. An example of a preferred embodiment of this altered form of the NIM1 gene, which encodes a gene product having both an N-terminal and a C-terminal deletion, is presented in SEQ ID NO:13. An exemplary dominant-negative form of the NIM1 protein with a C-terminal deletion is shown in SEQ ID NO:14. The present invention also encompasses altered forms of alleles of NIM1, wherein the coding sequence of such an allele hybridizes under the following conditions to the coding sequence set forth in SEQ ID NO:13: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:13 under the above conditions are altered so that the encoded product has both an N-terminal deletion, which removes lysine residues that may serve as potential ubiquitination sites in addition to the serines at amino acid positions corresponding to positions 55 and 59 of the wild-type gene product, as well as a C-terminal deletion, which removes serine and threonine residues.

In even another embodiment of the present invention, the NIM1 gene is altered so that the encoded product consists essentially of only the ankyrin domains of the wild-type gene product. An example of a preferred embodiment of this altered form of the NIM1 gene, which encodes the ankyrin domains, is presented in SEQ ID NO:15. An exemplary dominant-negative form of the NIM1 protein consists essentially of only the ankyrin domains is shown in SEQ ID NO:16. The present invention also encompasses altered forms of alleles of NIM1, wherein the coding sequence of such an allele hybridizes under the following conditions to the coding sequence set forth in SEQ ID NO:15: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:15 under the above conditions are altered so that the encoded product consists essentially of the ankyrin domains of the wild-type gene product.

Thus, the present invention concerns DNA molecules encoding altered forms of the NIM1 gene, such as those described above. The present invention also encompasses a chimeric gene comprising a promoter active in plants operatively linked to one of the above-described altered forms of the NIM1 gene, a recombinant vector comprising such a chimeric gene, wherein the vector is capable of being stably transformed into a host cell, as well as a host cell stably transformed with such a vector. Preferably, the host cell is a plant cell from, for example, one of the following agronomically important crops: rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The present invention is also directed to a method of conferring a CIM phenotype to a plant by transforming the plant with a recombinant vector comprising a chimeric gene that itself comprises a promoter active in plants operatively linked to one of the above-described altered forms of the NIM1 gene, wherein the encoded dominant-negative form of the NIM1 protein is expressed in the transformed plant and confers a CIM phenotype to the plant.

Further, the present invention is directed to a method of activating systemic acquired resistance in a plant by transforming the plant with a recombinant vector comprising a chimeric gene that itself comprises a promoter active in plants operatively linked to one of the above-described altered forms of the NIM1 gene, wherein the encoded dominant-negative form of the NIM1 protein is expressed in the transformed plant and activates systemic acquired resistance in the plant.

In addition, the present invention is directed to a method of conferring broad spectrum disease resistance to a plant by transforming the plant with a recombinant vector comprising a chimeric gene that itself comprises a promoter active in plants operatively linked to one of the above-described altered forms of the NIM1 gene, wherein the encoded dominant-negative form of the NIM1 protein is expressed in the transformed plant and confers broad spectrum disease resistance to the plant.

BRIEF DESCRIPTION OF THE DRAWINGS

FIGS. 1A–1B is a sequence alignment of the NIM1 protein sequence with IκBα from mouse, rat, and pig. Vertical bars (|) above the sequences indicate amino acid identity between NIM1 and the IκBα sequences (matrix score equals 1.5); double dots (:) above the sequences indicate a similarity score >0.5; single dots (.) above the sequences indicate a similarity score <0.5 but >0.0; and a score <0.0 indicates no similarity and has no indicia above the sequences (see Examples). Locations of the mammalian IκBα ankyrin domains were identified according to de Martin et al., Gene 152, 253–255 (1995). The dots within a sequence indicate gaps between NIM1 and IκBα proteins. The five ankyrin repeats in IκBα are indicated by the dashed lines under the sequence. Amino acids are numbered relative to the NIM1 protein with gaps introduced where appropriate. Plus signs (+) are placed above the sequences every 10 amino acids.

FIG. 2 is an amino acid sequence comparison of regions of the NIM1 protein (numbers correspond to amino acid positions in SEQ ID NO:2) and rice EST protein products (SEQ ID NOS: 17–24).

BRIEF DESCRIPTION OF THE SEQUENCES IN THE SEQUENCE LISTING

SEQ ID NO:1 is a 5655-bp genomic sequence comprising the coding region of the wild-type Arabidopsis thaliana NIM1 gene.

SEQ ID NO:2 is the amino acid sequence of the wild-type Arabidopsis thaliana NIM1 protein encoded by the coding region of SEQ ID NO:1.

Figure 1A:
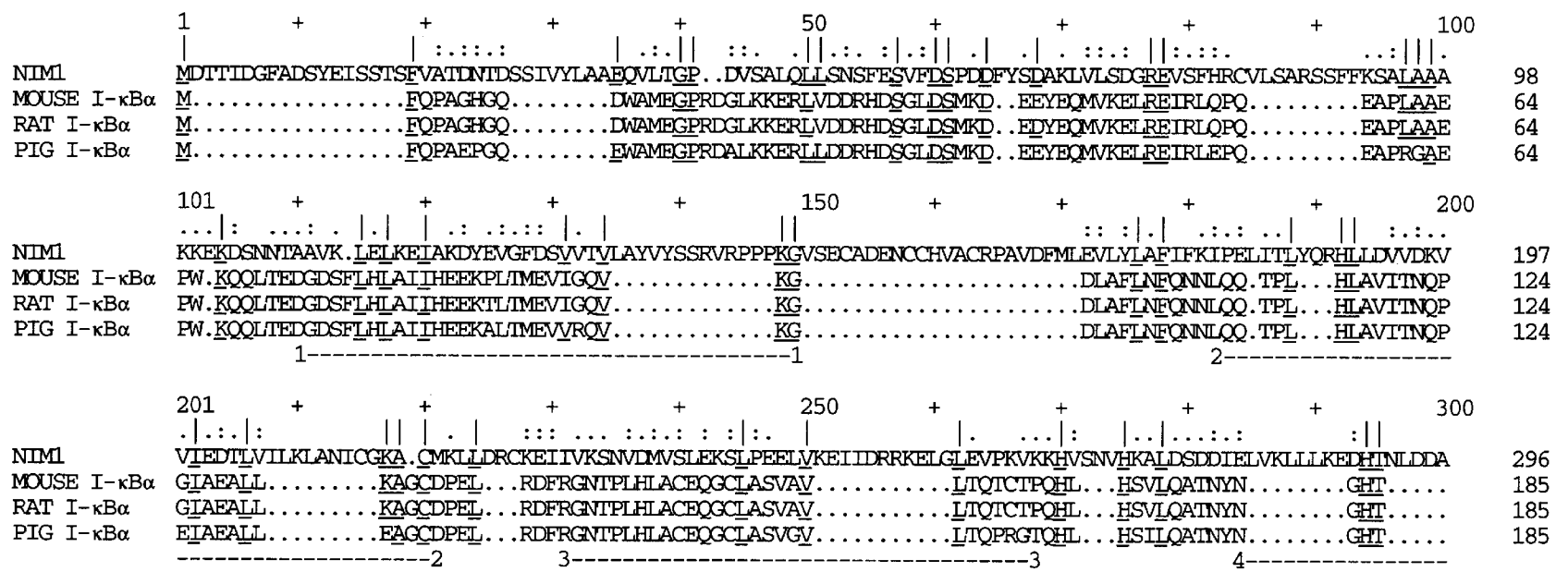

SEQ ID NO:3 is the mouse IκBα amino acid sequence from FIG. 1.

SEQ ID NO:4 is the rat IκBα amino acid sequence from FIG. 1.

SEQ ID NO:5 is the pig IκBα amino acid sequence from FIG. 1.

SEQ ID NO:6 is the cDNA sequence of the Arabidopsis thaliana NIM1 gene.

SEQ ID NOS:7 and 8 are the DNA coding sequence and encoded amino acid sequence, respectively, of a dominant-negative form of the NIM1 protein having alanine residues instead of serine residues at amino acid positions 55 and 59.

SEQ ID NOS:9 and 10 are the DNA coding sequence and encoded amino acid sequence, respectively, of a dominant-negative form of the NIM1 protein having an N-terminal deletion.

SEQ ID NOS:11 and 12 are the DNA coding sequence and encoded amino acid sequence, respectively, of a dominant-negative form of the NIM1 protein having a C-terminal deletion.

SEQ ID NOS:13 and 14 are the DNA coding sequence and encoded amino acid sequence, respectively, of an altered form of the NIM1 gene having both N-terminal and C-terminal amino acid deletions.

SEQ ID NOS:15 and 16 are the DNA coding sequence and encoded amino acid sequence, respectively, of the ankyrin domain of NIM1.

SEQ ID NO:17 is the Rice-1 AA sequence 33–155 from FIG. 2.

SEQ ID NO:18 is the Rice-1 AA sequence 215–328 from FIG. 2.

SEQ ID NO:19 is the Rice-2 AA sequence 33–155 from FIG. 2.

SEQ ID NO:20 is the Rice-2 AA sequence 208–288 from FIG. 2.

SEQ ID NO:21 is the Rice-3 AA sequence 33–155 from FIG. 2.

SEQ ID NO:22 is the Rice-3 AA sequence 208–288 from FIG. 2.

SEQ ID NO:23 is the Rice-4 AA sequence 33–155 from FIG. 2.

SEQ ID NO:24 is the Rice-4 AA sequence 215–271 from FIG. 2.

SEQ ID NOS:25 through 32 are oligonucleotide primers.

DEFINITIONS acd: accelerated cell death mutant plant
AFLP: Amplified Fragment Length Polymorphism
avrRpt2: avirulence gene Rpt2, isolated from Pseudomonas syringae
BAC: Bacterial Artificial Chromosome
BTH: benzo(1,2,3)thiadiazole-7-carbothioic acid S-methyl ester
CIM: Constitutive IMmunity phenotype (SAR is constitutively activated)
cim: constitutive immunity mutant plant
cM: centimorgans
cpr1: constitutive expresser of PR genes mutant plant
Col-O: Arabidopsis ecotype Columbia
ECs: Enzyme combinations Emwa: *Peronospora parasitica* isolate compatible in the Ws-O ecotype of Arabidopsis
EMS: ethyl methane sulfonate
INA: 2,6-dichloroisonicotinic acid
Ler: Arabidopsis ecotype *Landsberg erecta*
lsd: lesions simulating disease mutant plant
nahG: salicylate hydroxylase *Pseudomonas putida* that converts salicylic acid to catechol
NahG: Arabidopsis line transformed with nahG gene
ndr: non-race-specific disease resistance mutant plant
nim: non-inducible immunity mutant plant
NIM1: the wild type gene, involved in the SAR signal transduction cascade
NIM1: Protein encoded by the wild type NIM1 gene
nim1: mutant allele of NIM1, conferring disease susceptibility to the plant; also refers to mutant *Arabidopsis thaliana* plants having the nim1 mutant allele of NIM1
Noco: *Peronospora parasitica* isolate compatible in the Col-O ecotype of Arabidopsis
ORF: open reading frame
PCs: Primer combinations
PR: Pathogenesis Related
SA: salicylic acid
SAR: Systemic Acquired Resistance
SSLP: Simple Sequence Length Polymorphism
UDS: Universal Disease Susceptible phenotype
Wela: *Peronospora parasitica* isolate compatible in the Weiningen ecotype of Arabidopsis
Ws-O: Arabidopsis ecotype Issilewskija
WT: wild type
YAC: Yeast Artificial Chromosome

DETAILED DESCRIPTION OF THE INVENTION

The NIM1 Gene is a Homolog of IκBα

The NIM1 gene is a key component of the systemic acquired resistance (SAR) pathway in plants (Ryals et al.,1996). The NIM1 gene is associated with the activation of SAR by chemical and biological inducers and, in conjunction with such inducers, is required for SAR and SAR gene expression. The location of the NIM1 gene was determined by molecular biological analysis of the genome of mutant plants known to carry the mutant nim1 gene, which gives the host plants extreme sensitivity to a wide variety of pathogens and renders them unable to respond to pathogens and chemical inducers of SAR. The wildtype NIM1 gene of Arapidopsis has been mapped and sequenced (SEQ ID NO:1). The wild-type NIM1 gene product (SEQ ID NO:2) is involved in the signal transduction cascade leading to both SAR and gene-for-gene disease resistance in Arabidopsis (Ryals et al., 1997). Recombinant overexpression of the wild-type form of NIM1 gives rise to plants with a constitutive immunity (CIM) phenotype and therefore confers disease resistance in transgenic plants. Increased levels of the active NIM1 protein produce the same disease-resistance effect as chemical induction with inducing chemicals such as BTH, INA, and SA.

The sequence of the NIM1 gene (SEQ ID NO:1) was used in BLAST searches, and matches were identified based on homology of one rather highly conserved domain in the NIM1 gene sequence to ankyrin domains found in a number of proteins such as spectrins, ankyrins, NF-κB and IκB (Michaely and Bennett, *Trends Cell Biol.* 2, 127–129 (1992)). Beyond the ankyrin motif, however, conventional computer analysis did not detect other strong homologies, including homology to IκBα. Despite the failings of the computer programs, pair-wise visual inspections between the NIM1 protein (SEQ ID NO:2) and 70 known ankyrin-containing proteins were carried out, and striking similarities were found to members of the IκBα class of transcription regulators (Baeuerle and Baltimore 1996; Baldwin 1996). As shown in FIG. 1, the NIM1 protein (SEQ ID NO:2) shares significant homology with IκBα proteins from mouse, rat, and pig (SEQ ID NOS:3, 4, and 5, respectively).

NIM1 contains several important structural domains of IκBα throughout the entire length of the protein, including ankyrin domains (indicated by the dashed underscoring in FIG. 1), 2 amino-terminal serines (amino acids 55 and 59 of NIM1), a pair of lysines (amino acids 99 and 100 in NIM1) and an acidic C-terminus. Overall, NIM1 and IκBα share identity at 30% of the residues and conservative replacements at 50% of the residues. Thus, there is homology between IκBα and NIM1 throughout the proteins, with an overall similarity of 80%.

One way in which IκBα protein functions in signal transduction is by binding to the cytosolic transcription factor NF-κB and preventing it from entering the nucleus and altering transcription of target genes (Baeuerle and Baltimore, 1996; Baldwin, 1996). The target genes of NF-κB regulate (activate or inhibit) several cellular processes, including antiviral, antimicrobial and cell death responses (Baeuerle and Baltimore, 1996). When the signal transduction pathway is activated, IκkBα is phosphorylated at two serine residues (amino acids 32 and 36 of Mouse IκBα). This programs ubiquitination at a double lysine (amino acids 21 and 22 of Mouse IκBα). Following ubiquitination, the NF-κB/IκB complex is routed through the proteosome where IκBα is degraded and NF-κB is released to the nucleus.

The phosphorylated serine residues important in IκBα function are conserved in NIM1 within a large contiguous block of conserved sequence from amino acids 35 to 84 (FIG. 1). In contrast to IκBα, where the double lysine is located about 15 amino acids toward the N-terminus of the protein, in NIM1 a double lysine is located about 40 amino acids toward the C-terminal end. Furthermore, a high degree of homology exists between NIM1 and IκBα in the serine/threonine rich carboxy terminal region which has been shown to be important in basal turnover rate (Sun et al., *Mol. Cell. Biol.* 16, 1058–1065 (1996)). According to the present invention based on the analysis of structural homology and the presence of elements known to be important for IκBα function, NIM1 is expected to function like the IκBα, having analogous effects on plant gene regulation.

Plants containing the wild-type NIM1 gene when treated with inducer chemicals are predicted to have more NIM1 gene product (IκB homolog) or less phosphorylation of the NIM1 gene product (IκB homolog). In accordance with this model, the result is that the plant NF-κB homolog is kept out of the nucleus, and SAR gene expression and resistance responses are allowed to occur. In the nim1 mutant plants a non-functional NIM1 gene product is present. Therefore, in accordance with this model, the NF-κB homolog is free to go to the nucleus and repress resistance and SAR gene expression.

Consistent with this idea, animal cells treated with salicylic acid show increased stability/abundance of IκB and a reduction of active NF-κB in the nucleus (Kopp and Ghosh, 1994). Mutations of IκB are known that act as super-repressors or dominant-negatives (Britta-Mareen Traenckner et al., *EMBO* 14: 2876–2883 (1995); Brown et al., *Science* 267: 1485–1488 (1996); Brockman et al., *Molecular* and *Cellular Biology* 15: 2809–2818 (1995); Wang et al., *Science* 274: 784–787 (1996)). These mutant forms of IκB bind to NF-κB but are not phosphorylated or ubiquitinated and therefore are not degraded. NF-κB remains bound to the IκB and cannot move into the nucleus.

Altered Forms of the NIM1 Gene

In view of the above, the present invention encompasses altered forms of NIM1 that act as dominant-negative regulators of the SAR signal transduction pathway. Plants transformed with these dominant negative forms of NIM1 have the opposite phenotype as nim1 mutant plants in that the plants transformed with altered forms of NIM1 exhibit constitutive SAR gene expression and therefore a CIM phenotype. Because of the position the NIM1 gene holds in the SAR signal transduction pathway, it is expected that a number of alterations to the gene, beyond those specifically disclosed herein, will result in constitutive expression of SAR genes and, therefore, a CIM phenotype.

Phosphorylation of serine residues in human IκBα is required for stimulus activated degradation of IκBα thereby activating NF-κB. Mutagenesis of the serine residues (S32 and S36) in human IκBα to alanine residues inhibits stimulus-induced phosphorylation, thus blocking IκBα proteosome-mediated degradation (Traenckner et al., 1995; Brown et al., 1996; Brockman et al., 1995; Wang et al., 1996). This altered form of IκBα can function as a dominant-negative form by retaining NF-κB in the cytoplasm thereby blocking downstream signaling events. Based on the amino acid sequence comparison between NIM1 and IκB shown in FIG. 1, serines 55 (S55) and 59 (S59) in NIM1 (SEQ ID NO:2) are homologous to S32 and S36 in human IκBα. To construct dominant-negative forms of NIM1, the serines at amino acid positions 55 and 59 are mutagenized to alanine residues. Thus, in a preferred embodiment of the present invention, the NIM1 gene is altered so that the encoded product has alanines instead of serines in the amino acid positions corresponding to positions 55 and 59 of the Arabidopsis NIM1 amino acid sequence. The present invention also encompasses disease-resistant transgenic plants transformed with such an altered form of the NIM1 gene, as well as methods of using this altered form of the NIM1 gene to confer disease resistance and activate SAR gene expression in plants transformed therewith.

Deletion of amino acids 1–36 (Brockman et al., 1995; Sun et al., 1996) or 1–72 (Sun et al., 1996) of human IκBα, which includes ubiquination lysine residues K21 and K22 as well as phosphorylation sites S32 and S36, results in a dominant-negative IκBα phenotype in transfected human cell cultures. An N-terminal deletion of the first 125 amino acids of the NIM1 gene product will remove eight lysine residues which could serve as ubiquination sites as well as the putative phosphorylation sites at S55 and S59 discussed above. Thus, in a preferred embodiment of the present invention, the NIM1 gene is altered so that the encoded product is missing approximately the first 125 amino acids compared to the native Arabidopsis NIM1 amino acid sequence. The present invention also encompasses disease-resistant transgenic plants transformed with such an altered form of the NIM1 gene, as well as methods of using this altered form of the NIM1 gene to confer disease resistance and activate SAR gene expression in plants transformed therewith.

Deletion of amino acids 261–317 of human IκBα may result in enhanced intrinsic stability by blocking constitutive phosphorylation of serine and threonine residues in the C-terminus. This altered form of IκBα is expected to function as a dominant-negative form. A region rich in serine and threonine is present at amino acids 522–593 in the C-terminus of NIM1. Thus, in a preferred embodiment of the present invention, the NIM1 gene is altered so that the encoded product is missing approximately its C-terminal portion, including amino acides 522–593, compared to the native Arabidopsis NIM1 amino acid sequence. The present invention also encompasses disease-resistant transgenic plants transformed with such an altered form of the NIM1 gene, as well as methods of using this altered form of the NIM1 gene to confer disease resistance and activate SAR gene expression in plants transformed therewith.

In another embodiment of the present invention, altered forms of the NIM1 gene product are produced as a result of C-terminal and N-terminal segment deletions or chimeras. In yet another embodiment of the present invention, constructs comprising the ankyrin domains from the NIM1 gene are provided. The present invention encompasses disease-resistant transgenic plants transformed with such NIM1 chimera or ankyrin constructs, as well as methods of using these variants of the NIM1 gene to confer disease resistance and activate SAR gene expression in plants transformed therewith.

The present invention concerns DNA molecules encoding altered forms of the NIM1 gene such as those described above, expression vectors containing such DNA molecules, and plants and plant cells transformed therewith. The invention also concerns methods of activating SAR in plants and conferring to plants a CIM phenotype and broad spectrum disease resistance by transforming the plants with DNA molecules encoding altered forms of the NIM1 gene product. The present invention additionally concerns plants transformed with an altered form of the NIM1 gene.

Disease Resistance

Expression of altered forms of the NIM1 gene in plants results in immunity to a wide array of plant pathogens, which include, but are not limited to viruses or viroids, e.g. tobacco or cucumber mosaic virus, ringspot virus or necrosis virus, pelargonium leaf curl virus, red clover mottle virus, tomato bushy stunt virus, and like viruses; fungi, e.g. *Scleropthora macrospora, Sclerophthora rayissiae, Sclerospora graminicola, Peronosclerospora sorghi, Peronosclerospora philippinensis, Peronosclerospora sacchari* and *Peronosclerospora maydis, Puccinia sorphi, Puccinia polysora* and *Physopella zeae, Cercospora zeae-maydis, Colletotrichum graminicola, Fusarium monoliforme, Gibberella zeae, Exserohilum turcicum, Kabatiellu zeae, Erysiphe graminis, Septoria, Bipolaris maydis, Phythophthora parasitica*, and *Peronospora tabacina*; bacteria, e.g. *Pseudomonas syringae, Pseudomonas tabaci*, and *Erwinia stewartii*; insects such as aphids, e.g. *Myzus persicae*; and lepidoptera, e.g., Heliothus spp.; and nematodes, e.g., *Meloidogyne incognita*.

The methods of the present invention can be utilized to confer disease resistance to a wide variety of plants, including gymnosperms, monocots, and dicots. Although disease resistance can be conferred upon any plants falling within these broad classes, it is particularly useful in agronomically important crop plants, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. Transformed cells can be regenerated into whole plants such that the gene imparts disease resistance to the intact transgenic plants. The expression system can be modified so that the disease resistance gene is continuously or constitutively expressed.

Recombinant DNA Technology

The altered form of the NIM1 gene conferring disease resistance to plants by enhancing SAR gene expression can be incorporated in plant or bacterial cells using conventional recombinant DNA technology. Generally, this involves inserting DNA molecule encoding one of the altered forms of NIM1 described above into an expression system to which the DNA molecule is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgt11, λgt10 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the chosen form of the NIM1 gene activates SAR in the transgenic plants.

A. Requirements for Construction of Plant Expression Cassettes

Gene sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used. The following are non-limiting examples of promoters that may be used in the expression cassettes.

a. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or gene sequences (including microbial ORF sequences) within its polylinker for the purpose of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

b. Expression under a Chemically/Pathogen Regulatable Promoter:

The double 35S promoter in pCGN1761ENX may be replaced with any other promoter of choice which will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. *Plant Cell* 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Constitutive Expression, the Ubiquitin Promoter:

Ubiquitin is another gene product known to accumulate in many cell types and its promoter has been cloned from several species for use in transgenic plants (e.g. sunflower—Binet et al. Plant Science 79: 87–94 (1991) and maize—Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The ubiquitin promoter is suitable for gene expression in transgenic plants, especially monocotyledons. Suitable vectors are derivatives of pAHC25 or any of the transformation vectors described in this application, modified by the introduction of the appropriate ubiquitin promoter and/or intron sequences.

e. Root Specific Expression:

Another pattern of gene expression is root expression. A suitable root promoter is described by de Framond (*FEBS* 290: 103–106 (1991)) and also in the published patent application EP 0 452 269, which is herein incorporated by reference. This promoter is transferred to a suitable vector such as pCGN1761ENX for the insertion of a selected gene and subsequent transfer of the entire promoter-gene-terminator cassette to a transformation vector of interest.

f. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

g. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

h. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

B. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., *EMBO J*. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below, the construction of two typical vectors suitable for Agrobacterium transformation is described.

a. pCIB200 and pCIB2001:

The binary vectors pcIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB 10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. *EMBO J* 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

C. Transformation

Once the coding sequence of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells. Below are descriptions of representative techniques for transforming both dicotyledonous and monocotyledonous plants.

1. Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3: 2717–2722 (1984), Potrykus et al., Mol. Gen. Genet. 199: 169–177 (1985), Reich etal., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain, which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792, all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558(1993)) and Weeks etal. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

More recently, tranformation of monocotyledons using Agrobacterium has been described. See, WO 94/00977 and U.S. Pat. No. 5,591,616, both of which are incorporated herein by reference.

Breeding

The altered forms of the NIM1 gene of the present invention can be utilized to confer disease resistance to a wide variety of plant cells, including those of gymnosperms, monocots, and dicots. Although the gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The high-level expression of the NIM1 gene and mutants thereof necessary for constitutive expression of SAR genes, in combination with other characteristics important for production and quality, can be incorporated into plant lines through breeding. Breeding approaches and techniques are known in the art. See, for example, Welsh J. R., *Fundamentals of Plant Genetics and Breeding*, John Wiley & Sons, N.Y. (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, N.Y. (1986); and Wricke and Weber, *Quantitative Genetics and Selection Plant Breeding*, Walter de Gruyter and Co., Berlin (1986).

Disease Resistance Evaluation

Disease Resistance evaluation is performed by methods known in the art. For examples see, Uknes et al, (1993) Molecular Plant Microbe Interactions 6: 680–685; Gorlach et al., (1996) Plant Cell 8:629–643; Alexander et al., Proc. Natl. Acad. Sci. USA 90: 7327–7331.

A. *Phytophthora parasitica* (Black shank) Resistance Assay

Assays for resistance to

Phytophthora parasitica, the causative organism of black shank, are performed on six-week-old plants grown as described in Alexander et al., Proc. Natl. Acad. Sci. USA 90: 7327–7331. Plants are watered, allowed to drain well, and then inoculated by applying 10 ml of a sporangium suspension (300 sporangia/ml) to the soil. Inoculated plants are kept in a greenhouse maintained at 23–25° C. day temperature, and 20–22° C. night temperature. The wilt index used for the assay is as follows: 0=no symptoms; 1=no symptoms; 1=some sign of wilting, with reduced turgidity; 2=clear wilting symptoms, but no rotting or stunting; 3=clear wilting symptoms with stunting, but no apparent stem rot; 4=severe wilting, with visible stem rot and some damage to root system; 5=as for 4, but plants near death or dead, and with severe reduction of root system. All assays are scored blind on plants arrayed in a random design.

B. *Pseudomonas syringae* Resistance Assay

Pseudomonas syringae pv. tabaci strain #551 is injected into the two lower leaves of several 6–7-week-old plants at a concentration of $10^6$ or $3\times10^6$ per ml in $H_2O$. Six individual plants are evaluated at each time point. *Pseudomonas tabaci* infected plants are rated on a 5 point disease severity scale, 5=100% dead tissue, 0=no symptoms. A T-test (LSD) is conducted on the evaluations for each day and the groupings are indicated after the Mean disease rating value. Values followed by the same letter on that day of evaluation are not statistically significantly different.

C. *Cercospora nicotianae* Resistance Assay

A spore suspension of *Cercospora nicotianae* (ATCC #18366) (100,000–150,000 spores per ml) is sprayed to imminent run-off onto the surface of the leaves. The plants are maintained in 100% humidity for five days. Thereafter the plants are misted with water 5–10 times per day. Six individual plants are evaluated at each time point. *Cercospora nicotianae* is rated on a % leaf area showing disease symptoms basis. A T-test (LSD) is conducted on the evaluations for each day and the groupings are indicated after the Mean disease rating value. Values followed by the same letter on that day of evaluation are not statistically significantly different.

D. *Peronospora parasitica* Resistance Assay

Assays for resistance to *Peronospora parasitica* are performed on plants as described in Uknes et al, (1993). Plants are inoculated with a combatible isolate of *P. parasitica* by spraying with a conidial suspension (approximately $5\times10^4$ spores per milliliter). Inoculated plants are incubated under humid conditions at 17° C. in a growth chamber with a 14-hr day/10-hr night cycle. Plants are examined at 3–14 days, preferably 7–12 days, after inoculation for the presence of conidiophores. In addition, several plants from each treatment are randomly selected and stained with lactophenol-trypan blue (Keogh et al., *Trans. Br. Mycol. Soc.* 74: 329–333 (1980)) for microscopic examination.

EXAMPLES

The invention is illustrated in further detail by the following detailed procedures, preparations, and examples. The examples are for illustration only, and are not to be construed as limiting the scope of the present invention.

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

NIM1 is a Homolog of IκBα

A multiple sequence alignment between the protein gene products of NIM1 and IκB was perfonned by which it was determined that the NIM1 gene product is a homolog of IκBα (FIG. 1). Sequence homology searches were performed using BLAST (Altschul et al., *J. Mol. Biol.* 215, 403–410 (1990)). The multiple sequence alignment was constructed using Clustal V (Higgins et al., *CABIOS* 5,151–153 (1989)) as part of the Lasergene Biocomputing Software package from DNASTAR (Madison, Wis.). The sequences used in the alignment were NIM1 (SEQ ID NO:2), mouse IκKα (SEQ ID NO:3, GenBank Accession #: 1022734), rat IκBα (SEQ ID NO:4, GenBank accession Nos. 57674 and X63594; Tewari et al., *Nucleic Acids Res.* 20, 607 (1992)), and pig IκBα (SEQ ID NO:5, GenBank accession No. Z21968; de Martin et al., *EMBO J.* 12, 2773–2779 (1993); GenBank accession No. 517193, de Martin et al., *Gene* 152, 253–255 (1995)). Parameters used in the Clustal analysis were gap penalty of 10 and gap length penalty of 10. Evolutionary divergence distances were calculated using the PAM250 weight table (Dayhoff et al., "A model of evolutionary change in proteins. Matrices for detecting distant relationships." In *Atlas of Protein Sequence and Structure*, Vol. 5, Suppl. 3, M. O., Dayhoff, ed (National Biomedical Research Foundation, Washington, D.C.), pp. 345–358 (1978)). Residue similarity was calculated using a modified Dayhoff table (Schwartz and Dayhoff, "A model of evolutionary change in proteins." In *Atlas of Protein Sequence and Structure*, M. O. Dayhoff, ed (National Biomedical Research Foundation, Washington, D.C.) pp. 353–358 (1979); Gribskov and Burgess, *Nucleic Acids Res.* 14, 6745–6763 (1986)).

Homology searches indicate similarity of NIM1 to ankyrin domains of several proteins including: ankyrin, NF-κB and IκB. The best overall homology is to IκB and related molecules (FIG. 1). NIM1 contains 2 serines at amino acid positions 55 and 59; the serine at position 59 is in a context (D/ExxxxS) and position (N-terminal) consistent with a role in phosphorylation-dependent, ubiquitin-mediated, inducible degradation. All IκBα's have these N-terminal serines and they are required for inactivation of IκB and subsequent release of NF-κB. NIM1 has ankyrin domains (amino acids 262–290 and 323–371). Ankyrin domains are believed to be involved in protein-protein interactions and are a ubiquitous feature for IκB and NF-κB molecules. The C-termini of IκB's can be dissimilar. NIM1 has some homology to a QL-rich region (amino acids 491–499) found in the C-termini of some IκBs.

Example 2

Generation of Altered Forms of NIM1—Changes of Serine Residues 55 and 59 to Alanine Residues Phosphorylation of serine residues in human IκBα is required for stimulus-activated degradation of IκBα thereby activating NF-κB. Mutagenesis of the serine residues (S32-S36) in human IκBα to alanine residues inhibits stimulus-induced phosphorylation thus blocking IκBα proteosome-mediated degradation (E. Britta-Mareen Traenckner et al., *EMBO J*. 14: 2876–2883 (1995); Brown et al., *Science* 267:1485–1488 (1996); Brockman et al., *Molecular and Cellular Biology* 15: 2809–2818 (1995); Wang et al., *Science* 274:784–787 (1996)).

This altered form of IκBα functions as a dominant negative form by retaining NF-κB in the cytoplasm, thereby blocking downstream signaling events. Based on sequence comparisons between NIM1 and IκB, serines 55 (S55) and 59 (S59) of NIM1 are homologous to S32 and S36 in human IκBα. To construct dominant-negative forms of NIM1, the serines at amino acid positions 55 and 59 are mutagenized to alanine residues. This can be done by any method known to those skilled in the art, such as, for example, by using the QuikChange Site Directed Mutagenesis Kit (#200518:Strategene).

Using a full length NIM1 cDNA (SEQ ID NO:6) including 42 bp of 5' untranslated sequence (UTR) and 187 bp of 3' UTR, the mutagenized construct can be made per the manufacturer's instructions using the following primers (SEQ ID NO:6, positions 192–226): 5'-CAA CAG CTT CGA AGC CGT CTT TGA CGC GCC GGA TG-3' (SEQ ID NO:25) and 5'-CAT CCG GCG CGT CAA AGA CGG CTT CGA AGC TGT TG-3' (SEQ ID NO:26), where the underlined bases denote the mutations. The strategy is as follows: The NIM1 cDNA cloned into vector pSE936 (Elledge et al., *Proc. Nat. Acad. Sci. USA* 88:1731–1735 (1991)) is denatured and the primers containing the altered bases are annealed. DNA polymerase (Pfu) extends the primers by nonstrand-displacement resulting in nicked circular strands. DNA is subjected to restriction endonuclease digestion with DpnI, which only cuts methylated sites (nonmutagenized template DNA). The remaining circular dsDNA is transformed into *E.coli* strain XL1-Blue. Plasmids from resulting colonies are extracted and sequenced to verify the presence of the mutated bases and to confirm that no other mutations occurred.

The mutagenized NIM1 cDNA is digested with the restriction endonuclease EcoRI and cloned into pCGN1761 under the transcriptional regulation of the double 35S promoter of the cauliflower mosaic virus. The transformation cassette including the 35S promoter, NIM1 cDNA and tml terminator is released from pCGN1761 by partial restriction digestion with XbaI and ligated into the XbaI and ligated into the XbaI site of dephosphorylated pCIB200. SEQ ID NOS:7 and 8 show the DNA coding sequence and encoded amino acid sequence, respectively, of this altered form of the NIM1 gene.

The present invention also encompasses altered forms of alleles of NIM1, wherein the coding sequence of such an allele hybridizes under the following conditions to the coding sequence set forth in SEQ ID NO:7: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:7 under these conditions are altered so that the encoded product has alanines instead of serines in the amino acid positions that correspond to positions 55 and 59 of SEQ ID NO:7.

Example 3

Generation of Altered Forms of NIM1—N-terminal Deletion

Deletion of amino acids 1–36 (Brockman et al.; Sun et al.) or 1–72 (Sun et al.) of human IκBα, which includes K21, K22, S32 and S36, results in a dominant-negative IκBα phenotype in transfected human cell cultures. An N-terminal deletion of approximately the first 125 amino acids of the encoded product of the NIM1 cDNA removes eight lysine residues that may serve as potential ubiquitination sites and also removes putative phosphorylation sites at S55 and S59 (see Example 2). This altered gene construct may be produced by any means known to those skilled in the art. For example, using the method of Ho et al., *Gene* 77:51–59 (1989), a NIM1 form may be generated in which DNA encoding approximately the first 125 amino acids is deleted. The following primers produce a 1612-bp PCR product (SEQ ID NO:6: 418 to 2011): 5'-gg aat tca-ATG GAT TCG GTT GTG ACT GTT TTG-3' (SEQ ID NO:27) and 5'-gga att cTA CAA ATC TGT ATA CCA TTG G-3' (SEQ ID NO:28) in which the synthetic start codon is underlined (ATG) and EcoRI linker sequence is in lower case. Amplification of fragments utilizes a reaction mixture comprising 0.1 to 100 ng of template DNA, 10 mM Tris pH 8.3/50 mM KCl/2 mM MgCl$_2$/0.001% gelatin/0.25 mM each dNTP/0.2 mM of each primer and 1 unit rTth DNA polymerase in a final volume of 50 mL and a Perkin Elmer Cetus 9600 PCR machine. PCR conditions are as follows: 94° C. 3 min: 35× (94° C. 30 sec: 52° C. 1 min: 72° C. 2 min. The PCR product is cloned directly into the pCR2.1 vector (Invitrogen). The PCR-generated insert in the PCR vector is released by restriction endonuclease digestion using EcoRI and ligated into the EcoRI site of dephosphorylated pCGN1761, under the transcriptional regulation of the double 35S promoter. The construct is sequenced to verify the presence of the synthetic starting ATG and to confirm that no other mutations occurred during PCR. The transformation cassette including the 35S promoter, modified NIM1 cDNA and tml terminator is released from pCGN1761 by partial restriction digestion with XbaI and ligated into the XbaI site of pCIB200. SEQ ID NOS:9 and 10 show the DNA coding sequence and encoded amino acid sequence, respectively, of an altered form of the NIM1 gene having an N-terminal amino acid deletion.

The present invention also encompasses altered forms of alleles of NIM1, wherein the coding sequence of such an allele hybridizes under the following conditions to the coding sequence set forth in SEQ ID NO:9: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:9 under these conditions are altered so that the encoded product has an N-terminal deletion that removes lysine residues that may serve as potential ubiquitination sites in addition to the serines at amino acid positions corresponding to positions 55 and 59 of the wild-type gene product.

Example 4

Generation of Altered Forms of NIM1—C-terminal Deletion

The deletion of amino acids 261–317 of human IκBα is believed to result in enhanced intrinsic stability by blocking the constitutive phosphorylation of serine and threonine residues in the C-terminus. A region rich in serine and threonine is present at amino acids 522–593 in the C-terminus of NIM1. The C-terminal coding region of the NIM1 gene may be modified by deleting the nucleotide sequences which encode amino acids 522–593. Using the method of Ho et al. (1989), the C-terminal coding region and 3' UTR of the NIM1 cDNA (SEQ ID NO:6: 1606–2011) is deleted by PCR, generating a 1623 bp fragment using the following primers: 5'-cggaattcGATCTCTTTAATTTGTGAATTT C-3' (SEQ ID NO:29) and 5'-ggaattcTCAACAGTT CATAATCTGGTCG-3' (SEQ ID NO:30) in which a synthetic stop codon is underlined (TGA on complementary strand) and EcoRI linker sequences are in lower case. PCR reaction components are as previously described and cycling parameters are as follows: 94° C. 3 min: 35× (94° C. 30 sec: 52° C. 30 sec: 72° C. 2 min); 72° C. 10 min]. The PCR product is cloned directly into the pCR2.1 vector (Invitrogen). The PCR-generated insert in the PCR vector is released by restriction endonuclease digestion using EcoRI and ligated into the EcoRI site of dephosphorylated pCGN1761, which contains the double 35S promoter. The construct is sequenced to verify the presence of the synthetic in-frame stop codon and to confirm that no other mutations occurred during PCR. The transformation cassette including the promoter, modified NIM1 cDNA, and tml terminator is released from pCGN1761 by partial restriction digestion with XbaI and ligated into the XbaI site of dephosphorylated pCIB200. SEQ ID NOS:11 and 12 show the DNA coding sequence and encoded amino acid sequence, respectively, of an altered form of the NIM1 gene having a C-terminal amino acid deletion.

The present invention also encompasses altered forms of alleles of NIM1, wherein the coding sequence of such an allele hybridizes under the following conditions to the coding sequence set forth in SEQ ID NO:11: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:11 under the above conditions are altered so that the encoded product has a C-terminal deletion that removes serine and threonine residues.

Example 5

Generation of Altered Forms of NIM1—N-terminal/C-terminal Deletion Chimera

An N-terminal and C-terminal deletion form of NIM1 is generated using a unique KpnI restriction site at position 819 (SEQ ID NO:6). The N-terminal deletion form (Example 3) is restriction endonuclease digested with EcoRI/KpnI and the 415 bp fragment corresponding to the modified N-terminus is recovered by gel electrophoresis. Likewise, the C-terminal deletion form (Example 4) is restriction endonuclease digested with EcoRI/KpnI and the 790 bp fragment corresponding to the modified C-terminus is recovered by gel electrophoresis. The fragments are ligated at 15° C., digested with EcoRI to eliminate EcoRI concatemers and cloned into the EcoRI site of dephosphorylated pCGN1761. The N/C-terminal deletion form of NIM1 is under the transcriptional regulation of the double 35S promoter. Similarly, a chimeric form of NIM1 is generated which consists of the S55/S59 mutagenized putative phosphorylation sites (Example 2) fused to the C-terminal deletion (Example 4). The construct is generated as described above. The constructs are sequenced to verify the fidelity of the start and stop codons and to confirm that no mutations occurred during cloning. The respective transformation cassettes including the 35S promoter, NIM1 chimera and tml terminator are released from pCGN1761 by partial restriction digestion with XbaI and ligated into the XbaI site of dephosphorylated pCIB200. SEQ ID NOS:13 and 14 show the DNA coding sequence and encoded amino acid sequence, respectively, of an altered form of the NIM1 gene having both N-terminal and C-terminal amino acid deletions.

The present invention also encompasses altered forms of alleles of NIM1, wherein the coding sequence of such an allele hybridizes under the following conditions to the coding sequence set forth in SEQ ID NO:13: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO: 13 under the above conditions are altered so that the encoded product has both an N-terminal deletion, which removes lysine residues that may serve as potential ubiquitination sites in addition to the serines at amino acid positions corresponding to positions 55 and 59 of the wild-type gene product, as well as a C-terminal deletion, which removes serine and threonine residues.

Example 6

Generation of Altered Forms of NIM1—Ankyrin Domains

NIM1 exhibits homology to ankyrin motifs at approximately amino acids 103–362. Using the method of Ho et al. (1989), the DNA sequence encoding the putative ankyrin domains (SEQ ID NO:1: 3093–3951) is PCR amplified (conditions: 94° C. 3 min:35× (94° C. 30 sec: 62° C. 30 sec: 72° C. 2 min): 72° C. 10 min) from the NIM1 cDNA (SEQ ID NO:6: 349–1128) using the following primers: 5'-ggaattcaATGGACTCCAACAACACCGCCGC-3' (SEQ ID NO:31) and 5'-ggaattcTCAACCTTCCAAAGTTGCTTCTGATG-3' (SEQ ID NO:32). The resulting product is restriction endonuclease digested with EcoRI and then spliced into the EcoRI site of dephosphorylated pCGN1761 under the transcriptional regulation of the double 35S promoter. The construct is sequenced to verify the presence of the synthetic start codon (ATG), an in-frame stop codon (TGA) and to confirm that no other mutations occurred during PCR. The transformation cassette including the 35S promoter, ankyrin domains, and tml terminator is released from pCGN1761 by partial restriction digestion with XbaI and ligated into the XbaI site of dephosphorylated pCIB200. SEQ ID NOS:15 and 16 show the DNA coding sequence and encoded amino acid sequence, respectively, of the ankyrin domain of NIM1.

The present invention also encompasses altered forms of alleles of NIM1, wherein the coding sequence of such an allele hybridizes under the following conditions to the coding sequence set forth in SEQ ID NO:15: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In these embodiments, alleles of NIM1 hybridizing to SEQ ID NO:15 under the above conditions are altered so that the encoded product consists essentially of the ankyrin domains of the wild-type gene product.

Example 7

Construction of Chimeric Genes

To increase the likelihood of appropriate spatial and temporal expression of altered NIM1 forms, a 4407 bp HindIII/BamHI fragment (SEQ ID NO:1: bases 1249–5655)

and/or a 5655 bp EcoRV/BamHI fragment (SEQ ID NO:1: bases 1–5655) containing the NIM1 promoter and gene is used for the creation of the altered NIM1 forms in Examples 2–6 above. Although the construction steps may differ, the concepts are comparable to the examples previously described herein. Strong overexpression of the altered forms may potentially be lethal. Therefore, the altered forms of the NIM1 gene described in Examples 2–6 may be placed under the regulation of promoters other than the endogenous NIM1 promoter, including but not limited to the nos promoter or small subunit of Rubisco promoter. Likewise, the altered NIM1 forms may be expressed under the regulation of the pathogen-responsive promoter PR-1 (U.S. Pat. No. 5,614, 395). Such expression permits strong expression of the altered NIM1 forms only under pathogen attack or other SAR-activating conditions. Furthermore, disease resistance may be evident in the transformants expressing altered NIM1 forms under PR-1 promoter regulation when treated with concentrations of SAR activator compounds (i.e., BTH or INA) which normally do not activate SAR, thereby activating a feedback loop (Weymann et al., (1995) Plant Cell 7: 2013–2022).

Example 8

Transformation of Altered Forms of the NIM1 into Arabidopsis thaliana

The constructs generated (Examples 2–7) are moved into Agrobacterium tumefaciens by electroporation into strain GV3101. These constructs are used to transform Arabidopsis ecotypes Col-0 and Ws-0 by vacuum infiltration (Mindrinos et al., Cell 78, 1089–1099 (1994)) or by standard root transformation. Seed from these plants is harvested and allowed to germinate on agar plates with kanamycin (or another appropriate antibiotic) as selection agent. Only plantlets that are transformed can detoxify the selection agent and survive. Seedlings that survive the selection are transferred to soil and tested for a CIM (constitutive immunity) phenotype. Plants are evaluated for observable phenotypic differences compared to wild type plants.

Example 9

Assessment of CIM Phenotype in Plants Transformed with Altered Forms of NIM1

A leaf from each primary transformant is harvested, RNA is isolated (Verwoerd et al., 1989, Nuc Acid Res, 2362) and tested for constitutive PR-1 expression by RNA blot analysis (Uknes et al., 1992). Each transformant is evaluated for an enhanced disease resistance response indicative of constitutive SAR expression analysis (Uknes et al., 1992). Conidial suspensions of 5–10×10$^4$ spores/ml from two compatible P. parasitica isolates, Emwa and Noco (i.e. these fungal strains cause disease on wildtype Ws-0 and Col-0 plants, respectively), are prepared, and transformants are sprayed with the appropriate isolate depending on the ecotype of the transformant. Inoculated plants are incubated under high humidity for 7 days. Plants are disease rated at day 7 and a single leaf is harvested for RNA blot analysis utilizing a probe which provides a means to measure fungal infection.

Transformants that exhibit a CIM phenotype are taken to the T1 generation and homozygous plants are identified. Transformants are subjected to a battery of disease resistance tests as described below. Fungal infection with Noco and Emwa is repeated and leaves are stained with lactophenol blue to identify the presence of fungal hyphae as described in Dietrich et al., (1994). Transformants are infected with the bacterial pathogen Pseudomonas syringae DC3000 to evaluate the spectrum of resistance evident as described in Uknes et al. (1993). Uninfected plants are evaluated for both free and glucose-conjugated SA and leaves are stained with lactophenol blue to evaluate for the presence of microscopic lesions. Resistant plants are sexually crossed with SAR mutants such as NahG (U.S. Pat. No. 5,614,395) and ndr1 to establish the epistatic relationship of the resistance phenotype to other mutants and evaluate how these dominant-negative mutants of NIM1 may influence the SA-dependent feedback loop.

Example 10

Isolation of NIM1 Homologs

Using the NIM1 cDNA (SEQ ID NO:6) as a probe, homologs of Arabidopsis NIM1 are identified through screening genomic or cDNA libraries from different crops such as, but not limited to those listed below in Example 11. Standard techniques for accomplishing this include hybridization screening of plated DNA libraries (either plaques or colonies; see, e.g. Sambrook et al., Molecular Cloning, eds., Cold Spring Harbor Laboratory Press. (1989)) and amplification by PCR using oligonucleotide primers (see, e.g. Innis et al., PCR Protocols, a Guide to Methods and Applications eds., Academic Press (1990)). Homologs identified are genetically engineered into the expression vectors herein and transformed into the above listed crops. Transformants are evaluated for enhanced disease resistance using relevant pathogens of the crop plant being tested.

NIM1 homologs in the genomes of cucumber, tomato, tobacco, maize, wheat and barley have been detected by DNA blot analysis. Genomic DNA was isolated from cucumber, tomato, tobacco, maize, wheat and barley, restriction digested with the enzymes BamHI, HindIII, XbaI, or SalI, electrophoretically separated on 0.8% agarose gels and transferred to nylon membrane by capillary blotting. Following UV-crosslinking to affix the DNA, the membrane was hybridized under low stringency conditions [(1% BSA; 520 mM NaPO$_4$, pH7.2; 7% lauryl sulfate, sodium salt; 1 mM EDTA; 250 mM sodium chloride) at 55° C. for 18–24 h] with $^{32}$P-radiolabelled Arabidopsis thaliana NIM1 cDNA. Following hybridization the blots were washed under low stringency conditions [6×SSC for 15 min. (X3) 3×SSC for 15 min. (X1) at 55° C.; 1×SSC is 0.15M NaCl, 15 mM Na-citrate (pH7.0)] and exposed to X-ray film to visualize bands that correspond to NIM1.

In addition, expressed sequence tags (EST) identified with similarity to the NIM1 gene can be used to isolate homologues. For example, several rice expressed sequence tags (ESTs) have been identified with similarity to the NIM1 gene. A multiple sequence alignment was constructed using Clustal V (Higgins, Desmond G. and Paul M. Sharp (1989), Fast and sensitive multiple sequence alignments on a microcomputer, CABIOS 5:151–153) as part of the DNA* (1228 South Park Street, Madison Wis., 53715) Lasergene Biocomputing Software package for the Macintosh (1994). Certain regions of the NIM1 protein are homologous in amino acid sequence to 4 different rice cDNA protein products. The homologies were identified using the NIM1 sequences in a GenBank BLAST search. Comparisons of the regions of homology in NIM1 and the rice cDNA products are shown in FIG. 2 (See also, SEQ ID NO:2 and SEQ ID NOS:17–24). The NIM1 protein fragments show from 36 to 48% identical amino acid sequences with the 4 rice products. These rice EST's may be especially useful for isolation of NIM1 homologues from other monocots.

Homologues may be obtained by PCR. In this method, comparisons are made between known homologues (e.g., rice and Arabidopsis). Regions of high amino acid and DNA similarity or identity are then used to make PCR primers. Regions rich in amino acid residues M and W are best followed by regions rich in amino acid residues F, Y, C, H, Q, K and E because these amino acids are encoded by a limited number of codons. Once a suitable region is identified, primers for that region are made with a diversity of substitutions in the $3^{rd}$ codon position. This diversity of substitution in the third position may be constrained depending on the species that is being targeted. For example, because maize is GC rich, primers are designed that utilize a G or a C in the $3^{rd}$ position, if possible.

The PCR reaction is performed from cDNA or genomic DNA under a variety of standard conditions. When a band is apparent, it is cloned and/or sequenced to determine if it is a NIM1 homologue.

Example 11

Expression Altered Forms of NIM1 in Crop Plants

Those constructs conferring a CIM phenotype in Col-0 or Ws-0 are transformed into crop plants for evaluation. Alternatively, altered native NIM1 genes isolated from crops in the preceding example are put back into the respective crops. Although the NIM1 gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. Transformants are evaluated for enhanced disease resistance. In a preferred embodiment of the invention, the expression of the altered form of the NIM1 gene is at a level which is at least two-fold above the expression level of the native NIM1 gene in wild type plants and is preferably ten-fold above the wild type expression level.

---

What is claimed is:

1. An isolated DNA molecule, comprising a nucleotide sequence that encodes a protein comprising SEQ ID NO:2, except that said protein comprises at least one serine-to-alanine mutation.

2. An isolated DNA molecule according to claim 1, wherein said protein comprises serine-to-anlanine mutations in amino acid positions corresponding to positions 55 and 59 of SEQ ID NO:2.

3. An isolated DNA molecule according to claim 1, wherein said protein comprises the amino acid sequence shown in SEQ ID NO:8.

4. A chimeric gene comprising a promoter active in plants operatively linked to the DNA molecule of claim 1.

5. A recombinant vector comprising the chimeric gene of claim 4, wherein said vector is capable of being stably transformed into a host cell.

6. A host cell comprising the chimeric gene of claim 4.

7. The host cell of claim 6, which is a plant cell.

8. A method of increasing SAR gene expression in a plant, comprising transforming the plant with the chimeric gene of claim 4.

9. A method of enhancing disease resistance in a plant, comprising transforming the plant with the chimeric gene of claim 4.

10. A plant comprising a plant cell according to claim 9.

\* \* \* \* \*

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 5655 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: exon
      (B) LOCATION: 2787..3347
      (D) OTHER INFORMATION: /product= "1st exon of NIM1"

(ix) FEATURE:
      (A) NAME/KEY: exon
      (B) LOCATION: 3427..4162
      (D) OTHER INFORMATION: /product= "2nd exon of NIM1"

(ix) FEATURE:
      (A) NAME/KEY: exon
      (B) LOCATION: 4271..4474
      (D) OTHER INFORMATION: /product= "3rd exon of NIM1"

(ix) FEATURE:
      (A) NAME/KEY: exon
      (B) LOCATION: 4586..4866
      (D) OTHER INFORMATION: /product= "4th exon of NIM1"

(ix) FEATURE:
      (A) NAME/KEY: CDS
      (B) LOCATION: join(2787..3347, 3427..4162, 4271..4474, 4586..
          4866)

(xi) SEQUENCE DESCRIPTION: SEQ ID NO:1:

```
TGTGATGCAA GTCATGGGAT ATTGCTTTGT GTTAAGTATA CAAAACCATC ACGTGGATAC      60

ATAGTCTTCA AACCAACCAC TAAACAGTAT CAGGTCATAC CAAAGCCAGA AGTGAAGGGT     120
```

```
TGGGATATGT CATTGGGTTT AGCGGTAATC GGATTGAACC CTTTCCGGTA TAAAATACAA      180

AGGCTTTCGC AGTCTCGGCG TATGTGTATG TCTCGGGGTA TCTACCATTT GAATCACAGA      240

ACTTTTATGT GCGAAGTTTT CGATTCTGAT TCGTTACCT GGAAGAGATT AGAAAATTTG       300

CGTCTACCAA AAACAGACAG ATTAATTTTT TCCAACCCGA TACAAGTTTC GGGGTTCTTG      360

CATTGGATAT CACGGAACAA CAATGTGATC CGGTTTTGTC TCAAAACCGA AACTTGGTCC      420

TTCTTCCATA CTCCGAACTC TGATGTTTTC TCAGGATTAG TCAGATACGA AGGGAAGCTA     480

GGTGCTATTC GTCAGTGGAC AAACAAAGAT CAAGAAGATG TTCACGAGTT ATGGGTTTTA     540

AAGAGCAGTT TTGAAAAGTC GTGGGTTAAA GTGAAAGATA TTAAAAGCAT GGAGTAGAT     600

TTGATTACGT GGACTCCAAG CAACGACGTT GTATTGTTTC GTAGTAGTGA TCGTGGTTGC    660

CTCTACAACA TAAACGCAGA GAAGTTGAAT TTAGTTTATG CAAAAAAGA GGGATCTGAT     720

TGTTCTTTCG TTTGTTTTCC GTTTTGTTCT GATTACGAGA GGGTTGATCT GAACGGAAGA    780

AGCAACGGGC CGACACTTTA AAAAAAAAAT AAAAAAAATG GGCCGACAAA TGCAAACGTA    840

GTTGACAAGG ATCTCAAGTC TCAAGTCTCA ATTGGCTCGC TCATTGTGGG GCATAAATAT    900

ATCTAGTGAT GTTAATTGT TTTTTATAAG GTAAAAGGA ATATTGAATT TGTTTCTTA       960

GGTTTATGTA ATAATACCAA ACATTGTTTT ATGAATATTT AATCTGATTT TTTGGCTAGT   1020

TATTTTATTA TATCAAGGGT TCCTGTTTAT AGTTGAAAAC AGTTACTGTA TAGAAAATAG   1080

TGTCCCAATT TTCTCTCTTA AATAATATAT TAGTTAATAA AAGATATTTT AATATATTAG   1140

ATATACATAA TATCTAAAGC AACACATATT TAGACACAAC ACGTAATATC TTACTATTGT   1200

TTACATATAT TTATAGCTTA CCAATATAAC CCGTATCTAT GTTTTATAAG CTTTTATACA   1260

ATATATGTAC GGTATGCTGT CCACGTATAT ATATTCTCCA AAAAAACGC ATGGTACACA    1320

AAATTTATTA AATATTTGGC AATTGGGTGT TTATCTAAAG TTTATCACAA TATTTATCAA   1380

CTATAATAGA TGGTAGAAGA TAAAAAAATT ATATCAGATT GATTCAATTA AATTTTATAA   1440

TATATCATTT TAAAAAATTA ATTAAAAGAA AACTATTTCA TAAAATTGTT CAAAAGATAA   1500

TTAGTAAAAT TAATTAAATA TGTGATGCTA TTGAGTTATA GAGAGTTATT GTAAATTTAC   1560

TTAAAATCAT ACAAATCTTA TCCTAATTTA ACTTATCATT TAAGAAATAC AAAAGTAAAA   1620

AACGCGGAAA GCAATAATTT ATTTACCTTA TTATAACTCC TATATAAAGT ACTCTGTTTA   1680

TTCAACATAA TCTTACGTTG TTGTATTCAT AGGCATCTTT AACCTATCTT TTCATTTTCT   1740

GATCTCGATC GTTTTCGATC CAACAAAATG AGTCTACCGG TGAGGAACCA AGAGGTGATT   1800

ATGCAGATTC CTTCTTCTTC TCAGTTTCCA GCAACATCGA GTCCGGAAAA CACCAATCAA   1860

GTGAAGGATG AGCCAAATTT GTTTAGACGT GTTATGAATT TGCTTTTACG TCGTAGTTAT   1920

TGAAAAAGCT GATTTATCGC ATGATTCAGA ACGAGAAGTT GAAGGCAAAT AACTAAAGAA   1980

GTCTTTTATA TGTATACAAT AATTGTTTTT AAATCAAATC CTAATTAAAA AAATATATTC   2040

ATTATGACTT TCATGTTTTT AATGTAATTT ATTCCTATAT CTATAATGAT TTGTTGTGA    2100

AGAGCGTTTT CATTTGCTAT AGAACAAGGA GAATAGTTCC AGGAAATATT CGACTTGATT   2160

TAATTATAGT GTAAACATGC TGAACACTGA AAATTACTTT TTCAATAAAC GAAAATATA    2220

ATATACATTA CAAAACTTAT GTGAATAAAG CATGAAACTT AATATACGTT CCCTTTATCA   2280

TTTTACTTCA AAGAAAATAA ACAGAAATGT AACTTTCACA TGTAAATCTA ATTCTTAAAT   2340

TTAAAAAATA ATATTTATAT ATTTATATGA AAATAACGAA CCGGATGAAA ATAAATTTT    2400

ATATATTTAT ATCATCTCCA AATCTAGTTT GGTTCAGGGG CTTACCGAAC CGGATTGAAC   2460

TTCTCATATA CAAAAATTAG CAACACAAAA TGTCTCCGGT ATAAATACTA ACATTTATAA   2520
```

-continued

```
CCCGAACCGG TTTAGCTTCC TGTTATATCT TTTTAAAAAA GATCTCTGAC AAAGATTCCT    2580

TTCCTGGAAA TTTACCGGTT TTGGTGAAAT GTAAACCGTG GGACGAGGAT GCTTCTTCAT    2640

ATCTCACCAC CACTCTCGTT GACTTGACTT GGCTCTGCTC GTCAATGGTT ATCTTCGATC    2700

TTTAACCAAA TCCAGTTGAT AAGGTCTCTT CGTTGATTAG CAGAGATCTC TTTAATTTGT    2760

GAATTTCAAT TCATCGGAAC CTGTTG ATG GAC ACC ACC ATT GAT GGA TTC GCC    2813
                            Met Asp Thr Thr Ile Asp Gly Phe Ala
                            1               5

GAT TCT TAT GAA ATC AGC AGC ACT AGT TTC GTC GCT ACC GAT AAC ACC    2861
Asp Ser Tyr Glu Ile Ser Ser Thr Ser Phe Val Ala Thr Asp Asn Thr
 10              15                  20                  25

GAC TCC TCT ATT GTT TAT CTG GCC GCC GAA CAA GTA CTC ACC GGA CCT    2909
Asp Ser Ser Ile Val Tyr Leu Ala Ala Glu Gln Val Leu Thr Gly Pro
             30                  35                  40

GAT GTA TCT GCT CTG CAA TTG CTC TCC AAC AGC TTC GAA TCC GTC TTT    2957
Asp Val Ser Ala Leu Gln Leu Leu Ser Asn Ser Phe Glu Ser Val Phe
             45                  50                  55

GAC TCG CCG GAT GAT TTC TAC AGC GAC GCT AAG CTT GTT CTC TCC GAC    3005
Asp Ser Pro Asp Asp Phe Tyr Ser Asp Ala Lys Leu Val Leu Ser Asp
         60                  65                  70

GGC CGG GAA GTT TCT TTC CAC CGG TGC GTT TTG TCA GCG AGA AGC TCT    3053
Gly Arg Glu Val Ser Phe His Arg Cys Val Leu Ser Ala Arg Ser Ser
 75                  80                  85

TTC TTC AAG AGC GCT TTA GCC GCC GCT AAG AAG GAG AAA GAC TCC AAC    3101
Phe Phe Lys Ser Ala Leu Ala Ala Ala Lys Lys Glu Lys Asp Ser Asn
 90                  95                 100                 105

AAC ACC GCC GCC GTG AAG CTC GAG CTT AAG GAG ATT GCC AAG GAT TAC    3149
Asn Thr Ala Ala Val Lys Leu Glu Leu Lys Glu Ile Ala Lys Asp Tyr
                110                 115                 120

GAA GTC GGT TTC GAT TCG GTT GTG ACT GTT TTG GCT TAT GTT TAC AGC    3197
Glu Val Gly Phe Asp Ser Val Val Thr Val Leu Ala Tyr Val Tyr Ser
             125                 130                 135

AGC AGA GTG AGA CCG CCG CCT AAA GGA GTT TCT GAA TGC GCA GAC GAG    3245
Ser Arg Val Arg Pro Pro Pro Lys Gly Val Ser Glu Cys Ala Asp Glu
         140                 145                 150

AAT TGC TGC CAC GTG GCT TGC CGG CCG GCG GTG GAT TTC ATG TTG GAG    3293
Asn Cys Cys His Val Ala Cys Arg Pro Ala Val Asp Phe Met Leu Glu
 155                 160                 165

GTT CTC TAT TTG GCT TTC ATC TTC AAG ATC CCT GAA TTA ATT ACT CTC    3341
Val Leu Tyr Leu Ala Phe Ile Phe Lys Ile Pro Glu Leu Ile Thr Leu
 170                 175                 180                 185

TAT CAG GTAAAACACC ATCTGCATTA AGCTATGGTT ACACATTCAT GAATATGTTC    3397
Tyr Gln

TTACTTGAGT ACTTGTATTT GTATTTCAG AGG CAC TTA TTG GAC GTT GTA GAC    3450
                               Arg His Leu Leu Asp Val Val Asp
                                       190                 195

AAA GTT GTT ATA GAG GAC ACA TTG GTT ATA CTC AAG CTT GCT AAT ATA    3498
Lys Val Val Ile Glu Asp Thr Leu Val Ile Leu Lys Leu Ala Asn Ile
             200                 205                 210

TGT GGT AAA GCT TGT ATG AAG CTA TTG GAT AGA TGT AAA GAG ATT ATT    3546
Cys Gly Lys Ala Cys Met Lys Leu Leu Asp Arg Cys Lys Glu Ile Ile
         215                 220                 225

GTC AAG TCT AAT GTA GAT ATG GTT AGT CTT GAA AAG TCA TTG CCG GAA    3594
Val Lys Ser Asn Val Asp Met Val Ser Leu Glu Lys Ser Leu Pro Glu
     230                 235                 240

GAG CTT GTT AAA GAG ATA ATT GAT AGA CGT AAA GAG CTT GGT TTG GAG    3642
Glu Leu Val Lys Glu Ile Ile Asp Arg Arg Lys Glu Leu Gly Leu Glu
 245                 250                 255
```

```
GTA CCT AAA GTA AAG AAA CAT GTC TCG AAT GTA CAT AAG GCA CTT GAC        3690
Val Pro Lys Val Lys Lys His Val Ser Asn Val His Lys Ala Leu Asp
260             265                 270                 275

TCG GAT GAT ATT GAG TTA GTC AAG TTG CTT TTG AAA GAG GAT CAC ACC        3738
Ser Asp Asp Ile Glu Leu Val Lys Leu Leu Leu Lys Glu Asp His Thr
                280                 285                 290

AAT CTA GAT GAT GCG TGT GCT CTT CAT TTC GCT GTT GCA TAT TGC AAT        3786
Asn Leu Asp Asp Ala Cys Ala Leu His Phe Ala Val Ala Tyr Cys Asn
            295                 300                 305

GTG AAG ACC GCA ACA GAT CTT TTA AAA CTT GAT CTT GCC GAT GTC AAC        3834
Val Lys Thr Ala Thr Asp Leu Leu Lys Leu Asp Leu Ala Asp Val Asn
        310                 315                 320

CAT AGG AAT CCG AGG GGA TAT ACG GTG CTT CAT GTT GCT GCG ATG CGG        3882
His Arg Asn Pro Arg Gly Tyr Thr Val Leu His Val Ala Ala Met Arg
325                 330                 335

AAG GAG CCA CAA TTG ATA CTA TCT CTA TTG GAA AAA GGT GCA AGT GCA        3930
Lys Glu Pro Gln Leu Ile Leu Ser Leu Leu Glu Lys Gly Ala Ser Ala
340                 345                 350                 355

TCA GAA GCA ACT TTG GAA GGT AGA ACC GCA CTC ATG ATC GCA AAA CAA        3978
Ser Glu Ala Thr Leu Glu Gly Arg Thr Ala Leu Met Ile Ala Lys Gln
                360                 365                 370

GCC ACT ATG GCG GTT GAA TGT AAT AAT ATC CCG GAG CAA TGC AAG CAT        4026
Ala Thr Met Ala Val Glu Cys Asn Asn Ile Pro Glu Gln Cys Lys His
            375                 380                 385

TCT CTC AAA GGC CGA CTA TGT GTA GAA ATA CTA GAG CAA GAA GAC AAA        4074
Ser Leu Lys Gly Arg Leu Cys Val Glu Ile Leu Glu Gln Glu Asp Lys
        390                 395                 400

CGA GAA CAA ATT CCT AGA GAT GTT CCT CCC TCT TTT GCA GTG GCG GCC        4122
Arg Glu Gln Ile Pro Arg Asp Val Pro Pro Ser Phe Ala Val Ala Ala
405                 410                 415

GAT GAA TTG AAG ATG ACG CTG CTC GAT CTT GAA AAT AGA G                  4162
Asp Glu Leu Lys Met Thr Leu Leu Asp Leu Glu Asn Arg
420                 425                 430

GTATCTATCA AGTCTTATTT CTTATATGTT TGAATTAAAT TTATGTCCTC TCTATTAGGA      4222

AACTGAGTGA ACTAATGATA ACTATTCTTT GTGTCGTCCA CTGTTTAG   TT GCA CTT      4278
                                                         Val Ala Leu
                                                                 435

GCT CAA CGT CTT TTT CCA ACG GAA GCA CAA GCT GCA ATG GAG ATC GCC        4326
Ala Gln Arg Leu Phe Pro Thr Glu Ala Gln Ala Ala Met Glu Ile Ala
            440                 445                 450

GAA ATG AAG GGA ACA TGT GAG TTC ATA GTG ACT AGC CTC GAG CCT GAC        4374
Glu Met Lys Gly Thr Cys Glu Phe Ile Val Thr Ser Leu Glu Pro Asp
        455                 460                 465

CGT CTC ACT GGT ACG AAG AGA ACA TCA CCG GGT GTA AAG ATA GCA CCT        4422
Arg Leu Thr Gly Thr Lys Arg Thr Ser Pro Gly Val Lys Ile Ala Pro
    470                 475                 480

TTC AGA ATC CTA GAA GAG CAT CAA AGT AGA CTA AAA GCG CTT TCT AAA        4470
Phe Arg Ile Leu Glu Glu His Gln Ser Arg Leu Lys Ala Leu Ser Lys
485                 490                 495

ACC G GTATGGATTC TCACCCACTT CATCGGACTC CTTATCACAA AAAACAAAAC           4524
Thr
500

TAAATGATCT TTAAACATGG TTTTGTTACT TGCTGTCTGA CCTTGTTTTT TTTATCATCA      4584

G  TG GAA CTC GGG AAA CGA TTC TTC CCG CGC TGT TCG GCA GTG CTC          4629
   Val Glu Leu Gly Lys Arg Phe Phe Pro Arg Cys Ser Ala Val Leu
                505                 510                 515

GAC CAG ATT ATG AAC TGT GAG GAC TTG ACT CAA CTG GCT TGC GGA GAA        4677
Asp Gln Ile Met Asn Cys Glu Asp Leu Thr Gln Leu Ala Cys Gly Glu
                520                 525                 530
```

| | | | | | | | | | | | | | | |
|---|---|---|---|---|---|---|---|---|---|---|---|---|---|---|
| GAC | GAC | ACT | GCT | GAG | AAA | CGA | CTA | CAA | AAG | AAG | CAA | AGG | TAC | ATG | GAA | 4725 |
| Asp | Asp | Thr | Ala | Glu | Lys | Arg | Leu | Gln | Lys | Lys | Gln | Arg | Tyr | Met | Glu |
| | | | 535 | | | | | 540 | | | | | 545 | | |

| | | | | | | | | | | | | | | | |
|---|---|---|---|---|---|---|---|---|---|---|---|---|---|---|---|
| ATA | CAA | GAG | ACA | CTA | AAG | AAG | GCC | TTT | AGT | GAG | GAC | AAT | TTG | GAA | TTA | 4773 |
| Ile | Gln | Glu | Thr | Leu | Lys | Lys | Ala | Phe | Ser | Glu | Asp | Asn | Leu | Glu | Leu |
| | | 550 | | | | | 555 | | | | | 560 | | | |

| | | | | | | | | | | | | | | | |
|---|---|---|---|---|---|---|---|---|---|---|---|---|---|---|---|
| GGA | AAT | TCG | TCC | CTG | ACA | GAT | TCG | ACT | TCT | TCC | ACA | TCG | AAA | TCA | ACC | 4821 |
| Gly | Asn | Ser | Ser | Leu | Thr | Asp | Ser | Thr | Ser | Ser | Thr | Ser | Lys | Ser | Thr |
| 565 | | | | | 570 | | | | | 575 | | | | | |

| | | | | | | | | | | | | | | |
|---|---|---|---|---|---|---|---|---|---|---|---|---|---|---|
| GGT | GGA | AAG | AGG | TCT | AAC | CGT | AAA | CTC | TCT | CAT | CGT | CGT | CGG | TGA | 4866 |
| Gly | Gly | Lys | Arg | Ser | Asn | Arg | Lys | Leu | Ser | His | Arg | Arg | Arg | * |
| 580 | | | | | 585 | | | | | 590 | | | | |

```
GACTCTTGCC TCTTAGTGTA ATTTTTGCTG TACCATATAA TTCTGTTTTC ATGATGACTG    4926
TAACTGTTTA TGTCTATCGT TGGCGTCATA TAGTTTCGCT CTTCGTTTTG CATCCTGTGT    4986
ATTATTGCTG CAGGTGTGCT TCAAACAAAT GTTGTAACAA TTTGAACCAA TGGTATACAG    5046
ATTTGTAATA TATATTTATG TACATCAACA ATAACCCATG ATGGTGTTAC AGAGTTGCTA    5106
GAATCAAAGT GTGAAATAAT GTCAAATTGT TCATCTGTTG GATATTTTCC ACCAAGAACC    5166
AAAAGAATAT TCAAGTTCCC TGAACTTCTG GCAACATTCA TGTTATATGT ATCTTCCTAA    5226
TTCTTCCTTT AACCTTTTGT AACTCGAATT ACACAGCAAG TTAGTTTCAG GTCTAGAGAT    5286
AAGAGAACAC TGAGTGGGCG TGTAAGGTGC ATTCTCCTAG TCAGCTCCAT TGCATCCAAC    5346
ATTTGTGAAT GACACAAGTT AACAATCCTT TGCACCATTT CTGGGTGCAT ACATGGAAAC    5406
TTCTTCGATT GAAACTTCCC ACATGTGCAG GTGCGTTCGC TGTCACTGAT AGACCAAGAG    5466
ACTGAAAGCT TTCACAAATT GCCCTCAAAT CTTCTGTTTC TATCGTCATG ACTCCATATC    5526
TCCGACCACT GGTCATGAGC CAGAGCCCAC TGATTTTGAG GGAATTGGGC TAACCATTTC    5586
CGAGCTTCTG AGTCCTTCTT TTTGATGTCC TTTATGTAGG AATCAAATTC TTCCTTCTGA    5646
CTTGTGGAT                                                           5655
```

(2) INFORMATION FOR SEQ ID NO:2:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Thr Thr Ile Asp Gly Phe Ala Asp Ser Tyr Glu Ile Ser Ser
 1               5                  10                  15

Thr Ser Phe Val Ala Thr Asp Asn Thr Asp Ser Ser Ile Val Tyr Leu
            20                  25                  30

Ala Ala Glu Gln Val Leu Thr Gly Pro Asp Val Ser Ala Leu Gln Leu
        35                  40                  45

Leu Ser Asn Ser Phe Glu Ser Val Phe Asp Ser Pro Asp Asp Phe Tyr
    50                  55                  60

Ser Asp Ala Lys Leu Val Leu Ser Asp Gly Arg Glu Val Ser Phe His
65                  70                  75                  80

Arg Cys Val Leu Ser Ala Arg Ser Ser Phe Phe Lys Ser Ala Leu Ala
                85                  90                  95

Ala Ala Lys Lys Glu Lys Asp Ser Asn Asn Thr Ala Ala Val Lys Leu
            100                 105                 110

Glu Leu Lys Glu Ile Ala Lys Asp Tyr Glu Val Gly Phe Asp Ser Val
        115                 120                 125
```

-continued

| | | | | | | | | | | | | |
|---|---|---|---|---|---|---|---|---|---|---|---|---|
|Val|Thr|Val|Leu|Ala|Tyr|Val|Tyr|Ser|Ser|Arg|Val|Arg|Pro|Pro|Pro|
| | |130| | | |135| | | |140| | | | | |

Lys Gly Val Ser Glu Cys Ala Asp Glu Asn Cys Cys His Val Ala Cys
145             150             155             160

Arg Pro Ala Val Asp Phe Met Leu Glu Val Leu Tyr Leu Ala Phe Ile
                165             170             175

Phe Lys Ile Pro Glu Leu Ile Thr Leu Tyr Gln Arg His Leu Leu Asp
            180             185             190

Val Val Asp Lys Val Val Ile Glu Asp Thr Leu Val Ile Leu Lys Leu
            195             200             205

Ala Asn Ile Cys Gly Lys Ala Cys Met Lys Leu Leu Asp Arg Cys Lys
            210             215             220

Glu Ile Ile Val Lys Ser Asn Val Asp Met Val Ser Leu Glu Lys Ser
225             230             235             240

Leu Pro Glu Glu Leu Val Lys Glu Ile Ile Asp Arg Arg Lys Glu Leu
                245             250             255

Gly Leu Glu Val Pro Lys Val Lys His Val Ser Asn Val His Lys
                260             265             270

Ala Leu Asp Ser Asp Ile Glu Leu Val Lys Leu Leu Leu Lys Glu
            275             280             285

Asp His Thr Asn Leu Asp Asp Ala Cys Ala Leu His Phe Ala Val Ala
            290             295             300

Tyr Cys Asn Val Lys Thr Ala Thr Asp Leu Leu Lys Leu Asp Leu Ala
305             310             315             320

Asp Val Asn His Arg Asn Pro Arg Gly Tyr Thr Val Leu His Val Ala
                325             330             335

Ala Met Arg Lys Glu Pro Gln Leu Ile Leu Ser Leu Leu Glu Lys Gly
            340             345             350

Ala Ser Ala Ser Glu Ala Thr Leu Glu Gly Arg Thr Ala Leu Met Ile
            355             360             365

Ala Lys Gln Ala Thr Met Ala Val Glu Cys Asn Asn Ile Pro Glu Gln
            370             375             380

Cys Lys His Ser Leu Lys Gly Arg Leu Cys Val Glu Ile Leu Glu Gln
385             390             395             400

Glu Asp Lys Arg Glu Gln Ile Pro Arg Asp Val Pro Pro Ser Phe Ala
                405             410             415

Val Ala Ala Asp Glu Leu Lys Met Thr Leu Leu Asp Leu Glu Asn Arg
            420             425             430

Val Ala Leu Ala Gln Arg Leu Phe Pro Thr Glu Ala Gln Ala Ala Met
            435             440             445

Glu Ile Ala Glu Met Lys Gly Thr Cys Glu Phe Ile Val Thr Ser Leu
450             455             460

Glu Pro Asp Arg Leu Thr Gly Thr Lys Arg Thr Ser Pro Gly Val Lys
465             470             475             480

Ile Ala Pro Phe Arg Ile Leu Glu Glu His Gln Ser Arg Leu Lys Ala
                485             490             495

Leu Ser Lys Thr Val Glu Leu Gly Lys Arg Phe Pro Arg Cys Ser
            500             505             510

Ala Val Leu Asp Gln Ile Met Asn Cys Glu Asp Leu Thr Gln Leu Ala
            515             520             525

Cys Gly Glu Asp Asp Thr Ala Glu Lys Arg Leu Gln Lys Lys Gln Arg
530             535             540

Tyr Met Glu Ile Gln Glu Thr Leu Lys Lys Ala Phe Ser Glu Asp Asn
545             550             555             560

-continued

```
Leu Glu Leu Gly Asn Ser Ser Leu Thr Asp Ser Thr Ser Ser Thr Ser
                565                 570                 575
Lys Ser Thr Gly Gly Lys Arg Ser Asn Arg Lys Leu Ser His Arg Arg
            580                 585                 590
Arg
```

(2) INFORMATION FOR SEQ ID NO:3:

(i) SEQUENCE CHARACTERISTICS:
        (A) LENGTH: 314 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Met Phe Gln Pro Ala Gly His Gly Gln Asp Trp Ala Met Glu Gly Pro
 1               5                  10                  15
Arg Asp Gly Leu Lys Lys Glu Arg Leu Val Asp Asp Arg His Asp Ser
            20                  25                  30
Gly Leu Asp Ser Met Lys Asp Glu Glu Tyr Glu Gln Met Val Lys Glu
        35                  40                  45
Leu Arg Glu Ile Arg Leu Gln Pro Gln Glu Ala Pro Leu Ala Ala Glu
50                  55                  60
Pro Trp Lys Gln Gln Leu Thr Glu Asp Gly Asp Ser Phe Leu His Leu
65                  70                  75                  80
Ala Ile Ile His Glu Glu Lys Pro Leu Thr Met Glu Val Ile Gly Gln
                85                  90                  95
Val Lys Gly Asp Leu Ala Phe Leu Asn Phe Gln Asn Asn Leu Gln Gln
            100                 105                 110
Thr Pro Leu His Leu Ala Val Ile Thr Asn Gln Pro Gly Ile Ala Glu
        115                 120                 125
Ala Leu Leu Lys Ala Gly Cys Asp Pro Glu Leu Arg Asp Phe Arg Gly
130                 135                 140
Asn Thr Pro Leu His Leu Ala Cys Glu Gln Gly Cys Leu Ala Ser Val
145                 150                 155                 160
Ala Val Leu Thr Gln Thr Cys Thr Pro Gln His Leu His Ser Val Leu
                165                 170                 175
Gln Ala Thr Asn Tyr Asn Gly His Thr Cys Leu His Leu Ala Ser Thr
            180                 185                 190
His Gly Tyr Leu Ala Ile Val Glu His Leu Val Thr Leu Gly Ala Asp
        195                 200                 205
Val Asn Ala Gln Glu Pro Cys Asn Gly Arg Thr Ala Leu His Leu Ala
210                 215                 220
Val Asp Leu Gln Asn Pro Asp Leu Val Ser Leu Leu Leu Lys Cys Gly
225                 230                 235                 240
Ala Asp Val Asn Arg Val Thr Tyr Gln Gly Tyr Ser Pro Tyr Gln Leu
                245                 250                 255
Thr Trp Gly Arg Pro Ser Thr Arg Ile Gln Gln Gln Leu Gly Gln Leu
            260                 265                 270
Thr Leu Glu Asn Leu Gln Met Leu Pro Glu Ser Glu Asp Glu Glu Ser
        275                 280                 285
```

-continued

```
Tyr Asp Thr Glu Ser Glu Phe Thr Glu Asp Glu Leu Pro Tyr Asp Asp
    290                 295                 300

Cys Val Phe Gly Gly Gln Arg Leu Thr Leu
305                 310
```

(2) INFORMATION FOR SEQ ID NO:4:

(i) SEQUENCE CHARACTERISTICS:
        (A) LENGTH: 314 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

```
Met Phe Gln Pro Ala Gly His Gly Gln Asp Trp Ala Met Glu Gly Pro
1               5                   10                  15

Arg Asp Gly Leu Lys Lys Glu Arg Leu Val Asp Asp Arg His Asp Ser
            20                  25                  30

Gly Leu Asp Ser Met Lys Asp Glu Asp Tyr Glu Gln Met Val Lys Glu
        35                  40                  45

Leu Arg Glu Ile Arg Leu Gln Pro Gln Glu Ala Pro Leu Ala Ala Glu
50                  55                  60

Pro Trp Lys Gln Gln Leu Thr Glu Asp Gly Asp Ser Phe Leu His Leu
65                  70                  75                  80

Ala Ile Ile His Glu Glu Lys Thr Leu Thr Met Glu Val Ile Gly Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Gly Ile Ala Glu
        115                 120                 125

Ala Leu Leu Lys Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Ala Val Leu Thr Gln Thr Cys Thr Pro Gln His Leu His Ser Val Leu
                165                 170                 175

Gln Ala Thr Asn Tyr Asn Gly His Thr Cys Leu His Leu Ala Ser Ile
            180                 185                 190

His Gly Tyr Leu Gly Ile Val Glu His Leu Val Thr Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Thr Leu Pro Glu Ser Glu Asp Glu Glu Ser
        275                 280                 285

Tyr Asp Thr Glu Ser Glu Phe Thr Glu Asp Glu Leu Pro Tyr Asp Asp
    290                 295                 300

Cys Val Phe Gly Gly Gln Arg Leu Thr Leu
305                 310
```

(2) INFORMATION FOR SEQ ID NO:5:

(i) SEQUENCE CHARACTERISTICS:
        (A) LENGTH: 314 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:5:

```
Met Phe Gln Pro Ala Glu Pro Gly Gln Glu Trp Ala Met Glu Gly Pro
 1               5                  10                  15

Arg Asp Ala Leu Lys Lys Glu Arg Leu Leu Asp Asp Arg His Asp Ser
             20                  25                  30

Gly Leu Asp Ser Met Lys Asp Glu Glu Tyr Glu Gln Met Val Lys Glu
         35                  40                  45

Leu Arg Glu Ile Arg Leu Glu Pro Gln Glu Ala Pro Arg Gly Ala Glu
     50                  55                  60

Pro Trp Lys Gln Gln Leu Thr Glu Asp Gly Asp Ser Phe Leu His Leu
 65                  70                  75                  80

Ala Ile Ile His Glu Glu Lys Ala Leu Thr Met Glu Val Val Arg Gln
                 85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
        115                 120                 125

Ala Leu Leu Glu Ala Gly Cys Asp Pro Glu Leu Arg Asp Phe Arg Gly
    130                 135                 140

Asn Thr Pro Leu His Leu Ala Cys Glu Gln Gly Cys Leu Ala Ser Val
145                 150                 155                 160

Gly Val Leu Thr Gln Pro Arg Gly Thr Gln His Leu His Ser Ile Leu
                165                 170                 175

Gln Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Asp Glu Leu Pro Tyr Asp Asp
    290                 295                 300

Cys Val Leu Gly Gly Gln Arg Leu Thr Leu
305                 310
```

(2) INFORMATION FOR SEQ ID NO:6:

(i) SEQUENCE CHARACTERISTICS:
        (A) LENGTH: 2011 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
    (A) ORGANISM: Arabidopsis thaliana (ix) FEATURE:
    (A) NAME/KEY: misc_feature
    (B) LOCATION: 1..2011
    (D) OTHER INFORMATION: /note= "NIM1 cDNA sequence"

(ix) FEATURE:
    (A) NAME/KEY: CDS
    (B) LOCATION: 43..1824
    (D) OTHER INFORMATION: /product= "NIM1 protein"

(xi) SEQUENCE DESCRIPTION: SEQ ID NO:6:

```
GATCTCTTTA ATTTGTGAAT TTCAATTCAT CGGAACCTGT TG ATG GAC ACC ACC           54
                                                Met Asp Thr Thr
                                                 1

ATT GAT GGA TTC GCC GAT TCT TAT GAA ATC AGC AGC ACT AGT TTC GTC         102
Ile Asp Gly Phe Ala Asp Ser Tyr Glu Ile Ser Ser Thr Ser Phe Val
 5                  10                  15                  20

GCT ACC GAT AAC ACC GAC TCC TCT ATT GTT TAT CTG GCC GCC GAA CAA         150
Ala Thr Asp Asn Thr Asp Ser Ser Ile Val Tyr Leu Ala Ala Glu Gln
             25                  30                  35

GTA CTC ACC GGA CCT GAT GTA TCT GCT CTG CAA TTG CTC TCC AAC AGC         198
Val Leu Thr Gly Pro Asp Val Ser Ala Leu Gln Leu Leu Ser Asn Ser
         40                  45                  50

TTC GAA TCC GTC TTT GAC TCG CCG GAT GAT TTC TAC AGC GAC GCT AAG         246
Phe Glu Ser Val Phe Asp Ser Pro Asp Asp Phe Tyr Ser Asp Ala Lys
     55                  60                  65

CTT GTT CTC TCC GAC GGC CGG GAA GTT TCT TTC CAC CGG TGC GTT TTG         294
Leu Val Leu Ser Asp Gly Arg Glu Val Ser Phe His Arg Cys Val Leu
 70                  75                  80

TCA GCG AGA AGC TCT TTC TTC AAG AGC GCT TTA GCC GCC GCT AAG AAG         342
Ser Ala Arg Ser Ser Phe Phe Lys Ser Ala Leu Ala Ala Ala Lys Lys
 85                  90                  95                 100

GAG AAA GAC TCC AAC AAC ACC GCC GCC GTG AAG CTC GAG CTT AAG GAG         390
Glu Lys Asp Ser Asn Asn Thr Ala Ala Val Lys Leu Glu Leu Lys Glu
             105                 110                 115

ATT GCC AAG GAT TAC GAA GTC GGT TTC GAT TCG GTT GTG ACT GTT TTG         438
Ile Ala Lys Asp Tyr Glu Val Gly Phe Asp Ser Val Val Thr Val Leu
         120                 125                 130

GCT TAT GTT TAC AGC AGC AGA GTG AGA CCG CCG CCT AAA GGA GTT TCT         486
Ala Tyr Val Tyr Ser Ser Arg Val Arg Pro Pro Pro Lys Gly Val Ser
     135                 140                 145

GAA TGC GCA GAC GAG AAT TGC TGC CAC GTG GCT TGC CGG CCG GCG GTG         534
Glu Cys Ala Asp Glu Asn Cys Cys His Val Ala Cys Arg Pro Ala Val
 150                 155                 160

GAT TTC ATG TTG GAG GTT CTC TAT TTG GCT TTC ATC TTC AAG ATC CCT         582
Asp Phe Met Leu Glu Val Leu Tyr Leu Ala Phe Ile Phe Lys Ile Pro
165                 170                 175                 180

GAA TTA ATT ACT CTC TAT CAG AGG CAC TTA TTG GAC GTT GTA GAC AAA         630
Glu Leu Ile Thr Leu Tyr Gln Arg His Leu Leu Asp Val Val Asp Lys
             185                 190                 195

GTT GTT ATA GAG GAC ACA TTG GTT ATA CTC AAG CTT GCT AAT ATA TGT         678
Val Val Ile Glu Asp Thr Leu Val Ile Leu Lys Leu Ala Asn Ile Cys
         200                 205                 210

GGT AAA GCT TGT ATG AAG CTA TTG GAT AGA TGT AAA GAG ATT ATT GTC         726
Gly Lys Ala Cys Met Lys Leu Leu Asp Arg Cys Lys Glu Ile Ile Val
     215                 220                 225
```

-continued

| | | |
|---|---|---|
| AAG TCT AAT GTA GAT ATG GTT AGT CTT GAA AAG TCA TTG CCG GAA GAG<br>Lys Ser Asn Val Asp Met Val Ser Leu Glu Lys Ser Leu Pro Glu Glu<br>230                         235                     240 | | 774 |
| CTT GTT AAA GAG ATA ATT GAT AGA CGT AAA GAG CTT GGT TTG GAG GTA<br>Leu Val Lys Glu Ile Ile Asp Arg Arg Lys Glu Leu Gly Leu Glu Val<br>245                       250                       255                   260 | | 822 |
| CCT AAA GTA AAG AAA CAT GTC TCG AAT GTA CAT AAG GCA CTT GAC TCG<br>Pro Lys Val Lys Lys His Val Ser Asn Val His Lys Ala Leu Asp Ser<br>                     265                       270                   275 | | 870 |
| GAT GAT ATT GAG TTA GTC AAG TTG CTT TTG AAA GAG GAT CAC ACC AAT<br>Asp Asp Ile Glu Leu Val Lys Leu Leu Leu Lys Glu Asp His Thr Asn<br>               280                       285                   290 | | 918 |
| CTA GAT GAT GCG TGT GCT CTT CAT TTC GCT GTT GCA TAT TGC AAT GTG<br>Leu Asp Asp Ala Cys Ala Leu His Phe Ala Val Ala Tyr Cys Asn Val<br>             295                       300                   305 | | 966 |
| AAG ACC GCA ACA GAT CTT TTA AAA CTT GAT CTT GCC GAT GTC AAC CAT<br>Lys Thr Ala Thr Asp Leu Leu Lys Leu Asp Leu Ala Asp Val Asn His<br>310                       315                     320 | | 1014 |
| AGG AAT CCG AGG GGA TAT ACG GTG CTT CAT GTT GCT GCG ATG CGG AAG<br>Arg Asn Pro Arg Gly Tyr Thr Val Leu His Val Ala Ala Met Arg Lys<br>325                       330                     335                   340 | | 1062 |
| GAG CCA CAA TTG ATA CTA TCT CTA TTG GAA AAA GGT GCA AGT GCA TCA<br>Glu Pro Gln Leu Ile Leu Ser Leu Leu Glu Lys Gly Ala Ser Ala Ser<br>               345                       350                   355 | | 1110 |
| GAA GCA ACT TTG GAA GGT AGA ACC GCA CTC ATG ATC GCA AAA CAA GCC<br>Glu Ala Thr Leu Glu Gly Arg Thr Ala Leu Met Ile Ala Lys Gln Ala<br>             360                       365                   370 | | 1158 |
| ACT ATG GCG GTT GAA TGT AAT AAT ATC CCG GAG CAA TGC AAG CAT TCT<br>Thr Met Ala Val Glu Cys Asn Asn Ile Pro Glu Gln Cys Lys His Ser<br>             375                       380                   385 | | 1206 |
| CTC AAA GGC CGA CTA TGT GTA GAA ATA CTA GAG CAA GAA GAC AAA CGA<br>Leu Lys Gly Arg Leu Cys Val Glu Ile Leu Glu Gln Glu Asp Lys Arg<br>390                       395                     400 | | 1254 |
| GAA CAA ATT CCT AGA GAT GTT CCT CCC TCT TTT GCA GTG GCG GCC GAT<br>Glu Gln Ile Pro Arg Asp Val Pro Pro Ser Phe Ala Val Ala Ala Asp<br>405                       410                     415                   420 | | 1302 |
| GAA TTG AAG ATG ACG CTG CTC GAT CTT GAA AAT AGA GTT GCA CTT GCT<br>Glu Leu Lys Met Thr Leu Leu Asp Leu Glu Asn Arg Val Ala Leu Ala<br>               425                       430                   435 | | 1350 |
| CAA CGT CTT TTT CCA ACG GAA GCA CAA GCT GCA ATG GAG ATC GCC GAA<br>Gln Arg Leu Phe Pro Thr Glu Ala Gln Ala Ala Met Glu Ile Ala Glu<br>             440                       445                   450 | | 1398 |
| ATG AAG GGA ACA TGT GAG TTC ATA GTG ACT AGC CTC GAG CCT GAC CGT<br>Met Lys Gly Thr Cys Glu Phe Ile Val Thr Ser Leu Glu Pro Asp Arg<br>             455                       460                   465 | | 1446 |
| CTC ACT GGT ACG AAG AGA ACA TCA CCG GGT GTA AAG ATA GCA CCT TTC<br>Leu Thr Gly Thr Lys Arg Thr Ser Pro Gly Val Lys Ile Ala Pro Phe<br>470                       475                     480 | | 1494 |
| AGA ATC CTA GAA GAG CAT CAA AGT AGA CTA AAA GCG CTT TCT AAA ACC<br>Arg Ile Leu Glu Glu His Gln Ser Arg Leu Lys Ala Leu Ser Lys Thr<br>485                       490                     495                   500 | | 1542 |
| GTG GAA CTC GGG AAA CGA TTC TTC CCG CGC TGT TCG GCA GTG CTC GAC<br>Val Glu Leu Gly Lys Arg Phe Phe Pro Arg Cys Ser Ala Val Leu Asp<br>             505                       510                   515 | | 1590 |
| CAG ATT ATG AAC TGT GAG GAC TTG ACT CAA CTG GCT TGC GGA GAA GAC<br>Gln Ile Met Asn Cys Glu Asp Leu Thr Gln Leu Ala Cys Gly Glu Asp<br>             520                       525                   530 | | 1638 |
| GAC ACT GCT GAG AAA CGA CTA CAA AAG AAG CAA AGG TAC ATG GAA ATA<br>Asp Thr Ala Glu Lys Arg Leu Gln Lys Lys Gln Arg Tyr Met Glu Ile<br>             535                       540                   545 | | 1686 |

```
CAA GAG ACA CTA AAG AAG GCC TTT AGT GAG GAC AAT TTG GAA TTA GGA     1734
Gln Glu Thr Leu Lys Lys Ala Phe Ser Glu Asp Asn Leu Glu Leu Gly
550                 555                 560

AAT TTG TCC CTG ACA GAT TCG ACT TCT TCC ACA TCG AAA TCA ACC GGT     1782
Asn Leu Ser Leu Thr Asp Ser Thr Ser Ser Thr Ser Lys Ser Thr Gly
565                 570                 575                 580

GGA AAG AGG TCT AAC CGT AAA CTC TCT CAT CGT CGT CGG TGA             1824
Gly Lys Arg Ser Asn Arg Lys Leu Ser His Arg Arg Arg *
                585                 590

GACTCTTGCC TCTTAGTGTA ATTTTTGCTG TACCATATAA TTCTGTTTTC ATGATGACTG   1884

TAACTGTTTA TGTCTATCGT TGGCGTCATA TAGTTTCGCT CTTCGTTTTG CATCCTGTGT   1944

ATTATTGCTG CAGGTGTGCT TCAAACAAAT GTTGTAACAA TTTGAACCAA TGGTATACAG   2004

ATTTGTA                                                             2011

(2) INFORMATION FOR SEQ ID NO:7:

(i) SEQUENCE CHARACTERISTICS:
        (A) LENGTH: 2011 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 43..1824
        (D) OTHER INFORMATION: /product= "altered form of NIM1"
            /note= "Serine residues at amino acid positions 55 and
            59 in wild-type NIM1 gene product have been changed to
            Alanine residues."

(ix) FEATURE:
        (A) NAME/KEY: misc_feature
        (B) LOCATION: 205..217
        (D) OTHER INFORMATION: /note= "nucleotides 205 and 217
            changed from T's to G's compared to wild-type sequence."

(xi) SEQUENCE DESCRIPTION: SEQ ID NO:7:

GATCTCTTTA ATTTGTGAAT TTCAATTCAT CGGAACCTGT TG ATG GAC ACC ACC      54
                                              Met Asp Thr Thr
                                               1

ATT GAT GGA TTC GCC GAT TCT TAT GAA ATC AGC AGC ACT AGT TTC GTC    102
Ile Asp Gly Phe Ala Asp Ser Tyr Glu Ile Ser Ser Thr Ser Phe Val
 5                  10                  15                  20

GCT ACC GAT AAC ACC GAC TCC TCT ATT GTT TAT CTG GCC GCC GAA CAA    150
Ala Thr Asp Asn Thr Asp Ser Ser Ile Val Tyr Leu Ala Ala Glu Gln
                 25                  30                  35

GTA CTC ACC GGA CCT GAT GTA TCT GCT CTG CAA TTG CTC TCC AAC AGC    198
Val Leu Thr Gly Pro Asp Val Ser Ala Leu Gln Leu Leu Ser Asn Ser
             40                  45                  50

TTC GAA GCC GTC TTT GAC GCG CCG GAT GAT TTC TAC AGC GAC GCT AAG    246
Phe Glu Ala Val Phe Asp Ala Pro Asp Asp Phe Tyr Ser Asp Ala Lys
 55                  60                  65

CTT GTT CTC TCC GAC GGC CGG GAA GTT TCT TTC CAC CGG TGC GTT TTG    294
Leu Val Leu Ser Asp Gly Arg Glu Val Ser Phe His Arg Cys Val Leu
         70                  75                  80

TCA GCG AGA AGC TCT TTC TTC AAG AGC GCT TTA GCC GCC GCT AAG AAG    342
Ser Ala Arg Ser Ser Phe Phe Lys Ser Ala Leu Ala Ala Ala Lys Lys
85                   90                  95                 100

GAG AAA GAC TCC AAC AAC ACC GCC GCC GTG AAG CTC GAG CTT AAG GAG    390
Glu Lys Asp Ser Asn Asn Thr Ala Ala Val Lys Leu Glu Leu Lys Glu
                105                 110                 115
```

```
ATT GCC AAG GAT TAC GAA GTC GGT TTC GAT TCG GTT GTG ACT GTT TTG       438
Ile Ala Lys Asp Tyr Glu Val Gly Phe Asp Ser Val Val Thr Val Leu
        120                 125                 130

GCT TAT GTT TAC AGC AGC AGA GTG AGA CCG CCG CCT AAA GGA GTT TCT       486
Ala Tyr Val Tyr Ser Ser Arg Val Arg Pro Pro Pro Lys Gly Val Ser
            135                 140                 145

GAA TGC GCA GAC GAG AAT TGC TGC CAC GTG GCT TGC CGG CCG GCG GTG       534
Glu Cys Ala Asp Glu Asn Cys Cys His Val Ala Cys Arg Pro Ala Val
    150                 155                 160

GAT TTC ATG TTG GAG GTT CTC TAT TTG GCT TTC ATC TTC AAG ATC CCT       582
Asp Phe Met Leu Glu Val Leu Tyr Leu Ala Phe Ile Phe Lys Ile Pro
165                 170                 175                 180

GAA TTA ATT ACT CTC TAT CAG AGG CAC TTA TTG GAC GTT GTA GAC AAA       630
Glu Leu Ile Thr Leu Tyr Gln Arg His Leu Leu Asp Val Val Asp Lys
                185                 190                 195

GTT GTT ATA GAG GAC ACA TTG GTT ATA CTC AAG CTT GCT AAT ATA TGT       678
Val Val Ile Glu Asp Thr Leu Val Ile Leu Lys Leu Ala Asn Ile Cys
            200                 205                 210

GGT AAA GCT TGT ATG AAG CTA TTG GAT AGA TGT AAA GAG ATT ATT GTC       726
Gly Lys Ala Cys Met Lys Leu Leu Asp Arg Cys Lys Glu Ile Ile Val
        215                 220                 225

AAG TCT AAT GTA GAT ATG GTT AGT CTT GAA AAG TCA TTG CCG GAA GAG       774
Lys Ser Asn Val Asp Met Val Ser Leu Glu Lys Ser Leu Pro Glu Glu
    230                 235                 240

CTT GTT AAA GAG ATA ATT GAT AGA CGT AAA GAG CTT GGT TTG GAG GTA       822
Leu Val Lys Glu Ile Ile Asp Arg Arg Lys Glu Leu Gly Leu Glu Val
245                 250                 255                 260

CCT AAA GTA AAG AAA CAT GTC TCG AAT GTA CAT AAG GCA CTT GAC TCG       870
Pro Lys Val Lys Lys His Val Ser Asn Val His Lys Ala Leu Asp Ser
                265                 270                 275

GAT GAT ATT GAG TTA GTC AAG TTG CTT TTG AAA GAG GAT CAC ACC AAT       918
Asp Asp Ile Glu Leu Val Lys Leu Leu Leu Lys Glu Asp His Thr Asn
            280                 285                 290

CTA GAT GAT GCG TGT GCT CTT CAT TTC GCT GTT GCA TAT TGC AAT GTG       966
Leu Asp Asp Ala Cys Ala Leu His Phe Ala Val Ala Tyr Cys Asn Val
        295                 300                 305

AAG ACC GCA ACA GAT CTT TTA AAA CTT GAT CTT GCC GAT GTC AAC CAT      1014
Lys Thr Ala Thr Asp Leu Leu Lys Leu Asp Leu Ala Asp Val Asn His
    310                 315                 320

AGG AAT CCG AGG GGA TAT ACG GTG CTT CAT GTT GCT GCG ATG CGG AAG      1062
Arg Asn Pro Arg Gly Tyr Thr Val Leu His Val Ala Ala Met Arg Lys
325                 330                 335                 340

GAG CCA CAA TTG ATA CTA TCT CTA TTG GAA AAA GGT GCA AGT GCA TCA      1110
Glu Pro Gln Leu Ile Leu Ser Leu Leu Glu Lys Gly Ala Ser Ala Ser
                345                 350                 355

GAA GCA ACT TTG GAA GGT AGA ACC GCA CTC ATG ATC GCA AAA CAA GCC      1158
Glu Ala Thr Leu Glu Gly Arg Thr Ala Leu Met Ile Ala Lys Gln Ala
            360                 365                 370

ACT ATG GCG GTT GAA TGT AAT AAT ATC CCG GAG CAA TGC AAG CAT TCT      1206
Thr Met Ala Val Glu Cys Asn Asn Ile Pro Glu Gln Cys Lys His Ser
        375                 380                 385

CTC AAA GGC CGA CTA TGT GTA GAA ATA CTA GAG CAA GAA GAC AAA CGA      1254
Leu Lys Gly Arg Leu Cys Val Glu Ile Leu Glu Gln Glu Asp Lys Arg
    390                 395                 400

GAA CAA ATT CCT AGA GAT GTT CCT CCC TCT TTT GCA GTG GCG GCC GAT      1302
Glu Gln Ile Pro Arg Asp Val Pro Pro Ser Phe Ala Val Ala Ala Asp
405                 410                 415                 420

GAA TTG AAG ATG ACG CTG CTC GAT CTT GAA AAT AGA GTT GCA CTT GCT      1350
Glu Leu Lys Met Thr Leu Leu Asp Leu Glu Asn Arg Val Ala Leu Ala
                425                 430                 435
```

-continued

| | |
|---|---|
| CAA CGT CTT TTT CCA ACG GAA GCA CAA GCT GCA ATG GAG ATC GCC GAA<br>Gln Arg Leu Phe Pro Thr Glu Ala Gln Ala Ala Met Glu Ile Ala Glu<br>440                     445                     450 | 1398 |
| ATG AAG GGA ACA TGT GAG TTC ATA GTG ACT AGC CTC GAG CCT GAC CGT<br>Met Lys Gly Thr Cys Glu Phe Ile Val Thr Ser Leu Glu Pro Asp Arg<br>          455                     460                     465 | 1446 |
| CTC ACT GGT ACG AAG AGA ACA TCA CCG GGT GTA AAG ATA GCA CCT TTC<br>Leu Thr Gly Thr Lys Arg Thr Ser Pro Gly Val Lys Ile Ala Pro Phe<br>470                     475                     480 | 1494 |
| AGA ATC CTA GAA GAG CAT CAA AGT AGA CTA AAA GCG CTT TCT AAA ACC<br>Arg Ile Leu Glu Glu His Gln Ser Arg Leu Lys Ala Leu Ser Lys Thr<br>485                     490                     495                     500 | 1542 |
| GTG GAA CTC GGG AAA CGA TTC TTC CCG CGC TGT TCG GCA GTG CTC GAC<br>Val Glu Leu Gly Lys Arg Phe Phe Pro Arg Cys Ser Ala Val Leu Asp<br>          505                     510                     515 | 1590 |
| CAG ATT ATG AAC TGT GAG GAC TTG ACT CAA CTG GCT TGC GGA GAA GAC<br>Gln Ile Met Asn Cys Glu Asp Leu Thr Gln Leu Ala Cys Gly Glu Asp<br>520                     525                     530 | 1638 |
| GAC ACT GCT GAG AAA CGA CTA CAA AAG AAG CAA AGG TAC ATG GAA ATA<br>Asp Thr Ala Glu Lys Arg Leu Gln Lys Lys Gln Arg Tyr Met Glu Ile<br>535                     540                     545 | 1686 |
| CAA GAG ACA CTA AAG AAG GCC TTT AGT GAG GAC AAT TTG GAA TTA GGA<br>Gln Glu Thr Leu Lys Lys Ala Phe Ser Glu Asp Asn Leu Glu Leu Gly<br>550                     555                     560 | 1734 |
| AAT TTG TCC CTG ACA GAT TCG ACT TCT TCC ACA TCG AAA TCA ACC GGT<br>Asn Leu Ser Leu Thr Asp Ser Thr Ser Ser Thr Ser Lys Ser Thr Gly<br>565                     570                     575                     580 | 1782 |
| GGA AAG AGG TCT AAC CGT AAA CTC TCT CAT CGT CGT CGG TGA<br>Gly Lys Arg Ser Asn Arg Lys Leu Ser His Arg Arg Arg *<br>          585                     590 | 1824 |
| GACTCTTGCC TCTTAGTGTA ATTTTTGCTG TACCATATAA TTCTGTTTTC ATGATGACTG | 1884 |
| TAACTGTTTA TGTCTATCGT TGGCGTCATA TAGTTTCGCT CTTCGTTTTG CATCCTGTGT | 1944 |
| ATTATTGCTG CAGGTGTGCT TCAAACAAAT GTTGTAACAA TTTGAACCAA TGGTATACAG | 2004 |
| ATTTGTA | 2011 |

(2) INFORMATION FOR SEQ ID NO:8:

(i) SEQUENCE CHARACTERISTICS:
        (A) LENGTH:  593 amino acids
        (B) TYPE: amino acid
        (D) TOPOLOGY: linear (ii) MOLECULE TYPE: protein (xi) SEQUENCE DESCRIPTION: SEQ ID NO:8:

Met Asp Thr Thr Ile Asp Gly Phe Ala Asp Ser Tyr Glu Ile Ser Ser
 1               5                  10                  15

Thr Ser Phe Val Ala Thr Asp Asn Thr Asp Ser Ile Val Tyr Leu
            20                  25                  30

Ala Ala Glu Gln Val Leu Thr Gly Pro Asp Val Ser Ala Leu Gln Leu
        35                  40                  45

Leu Ser Asn Ser Phe Glu Ala Val Phe Asp Ala Pro Asp Asp Phe Tyr
    50                  55                  60

Ser Asp Ala Lys Leu Val Leu Ser Asp Gly Arg Glu Val Ser Phe His
65                  70                  75                  80

Arg Cys Val Leu Ser Ala Arg Ser Ser Phe Phe Lys Ser Ala Leu Ala
                85                  90                  95

Ala Ala Lys Lys Glu Lys Asp Ser Asn Asn Thr Ala Ala Val Lys Leu
            100                 105                 110

```
Glu Leu Lys Glu Ile Ala Lys Asp Tyr Glu Val Gly Phe Asp Ser Val
            115                 120                 125

Val Thr Val Leu Ala Tyr Val Tyr Ser Ser Arg Val Arg Pro Pro Pro
    130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
            180                 185                 190

Val Val Asp Lys Val Val Ile Glu Asp Thr Leu Val Ile Leu Lys Leu
        195                 200                 205

Ala Asn Ile Cys Gly Lys Ala Cys Met Lys Leu Leu Asp Arg Cys Lys
    210                 215                 220

Glu Ile Ile Val Lys Ser Asn Val Asp Met Val Ser Leu Glu Lys Ser
225                 230                 235                 240

Leu Pro Glu Glu Leu Val Lys Glu Ile Ile Asp Arg Arg Lys Glu Leu
                245                 250                 255

Gly Leu Glu Val Pro Lys Val Lys Lys His Val Ser Asn Val His Lys
            260                 265                 270

Ala Leu Asp Ser Asp Ile Glu Leu Val Lys Leu Leu Leu Lys Glu
    275                 280                 285

Asp His Thr Asn Leu Asp Asp Ala Cys Ala Leu His Phe Ala Val Ala
    290                 295                 300

Tyr Cys Asn Val Lys Thr Ala Thr Asp Leu Leu Lys Leu Asp Leu Ala
305                 310                 315                 320

Asp Val Asn His Arg Asn Pro Arg Gly Tyr Thr Val Leu His Val Ala
                325                 330                 335

Ala Met Arg Lys Glu Pro Gln Leu Ile Leu Ser Leu Leu Glu Lys Gly
            340                 345                 350

Ala Ser Ala Ser Glu Ala Thr Leu Glu Gly Arg Thr Ala Leu Met Ile
    355                 360                 365

Ala Lys Gln Ala Thr Met Ala Val Glu Cys Asn Asn Ile Pro Glu Gln
    370                 375                 380

Cys Lys His Ser Leu Lys Gly Arg Leu Cys Val Glu Ile Leu Glu Gln
385                 390                 395                 400

Glu Asp Lys Arg Glu Gln Ile Pro Arg Asp Val Pro Pro Ser Phe Ala
                405                 410                 415

Val Ala Ala Asp Glu Leu Lys Met Thr Leu Leu Asp Leu Glu Asn Arg
            420                 425                 430

Val Ala Leu Ala Gln Arg Leu Phe Pro Thr Glu Ala Gln Ala Ala Met
    435                 440                 445

Glu Ile Ala Glu Met Lys Gly Thr Cys Glu Phe Ile Val Thr Ser Leu
    450                 455                 460

Glu Pro Asp Arg Leu Thr Gly Thr Lys Arg Thr Ser Pro Gly Val Lys
465                 470                 475                 480

Ile Ala Pro Phe Arg Ile Leu Glu Glu His Gln Ser Arg Leu Lys Ala
                485                 490                 495

Leu Ser Lys Thr Val Glu Leu Gly Lys Arg Phe Phe Pro Arg Cys Ser
            500                 505                 510

Ala Val Leu Asp Gln Ile Met Asn Cys Glu Asp Leu Thr Gln Leu Ala
    515                 520                 525
```

```
Cys Gly Glu Asp Asp Thr Ala Glu Lys Arg Leu Gln Lys Lys Gln Arg
    530                 535                 540

Tyr Met Glu Ile Gln Glu Thr Leu Lys Lys Ala Phe Ser Glu Asp Asn
545                 550                 555                 560

Leu Glu Leu Gly Asn Leu Ser Leu Thr Asp Ser Thr Ser Ser Thr Ser
                565                 570                 575

Lys Ser Thr Gly Gly Lys Arg Ser Asn Arg Lys Leu Ser His Arg Arg
            580                 585                 590

Arg (2) INFORMATION FOR SEQ ID NO:9:

(i) SEQUENCE CHARACTERISTICS:
        (A) LENGTH: 1597 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1410
        (D) OTHER INFORMATION: /product= "Altered form of NIM1"
            /note= "N-terminal deletion compared to wild-type NIM1
            sequence."

(xi) SEQUENCE DESCRIPTION: SEQ ID NO:9:
```

| | | |
|---|---|---|
| ATG GAT TCG GTT GTG ACT GTT TTG GCT TAT GTT TAC AGC AGC AGA GTG<br>Met Asp Ser Val Val Thr Val Leu Ala Tyr Val Tyr Ser Ser Arg Val<br>1               5                   10                  15 | | 48 |
| AGA CCG CCG CCT AAA GGA GTT TCT GAA TGC GCA GAC GAG AAT TGC TGC<br>Arg Pro Pro Pro Lys Gly Val Ser Glu Cys Ala Asp Glu Asn Cys Cys<br>                20                  25                  30 | | 96 |
| CAC GTG GCT TGC CGG CCG GCG GTG GAT TTC ATG TTG GAG GTT CTC TAT<br>His Val Ala Cys Arg Pro Ala Val Asp Phe Met Leu Glu Val Leu Tyr<br>            35                  40                  45 | | 144 |
| TTG GCT TTC ATC TTC AAG ATC CCT GAA TTA ATT ACT CTC TAT CAG AGG<br>Leu Ala Phe Ile Phe Lys Ile Pro Glu Leu Ile Thr Leu Tyr Gln Arg<br>        50                  55                  60 | | 192 |
| CAC TTA TTG GAC GTT GTA GAC AAA GTT GTT ATA GAG GAC ACA TTG GTT<br>His Leu Leu Asp Val Val Asp Lys Val Val Ile Glu Asp Thr Leu Val<br>65                  70                  75                  80 | | 240 |
| ATA CTC AAG CTT GCT AAT ATA TGT GGT AAA GCT TGT ATG AAG CTA TTG<br>Ile Leu Lys Leu Ala Asn Ile Cys Gly Lys Ala Cys Met Lys Leu Leu<br>                85                  90                  95 | | 288 |
| GAT AGA TGT AAA GAG ATT ATT GTC AAG TCT AAT GTA GAT ATG GTT AGT<br>Asp Arg Cys Lys Glu Ile Ile Val Lys Ser Asn Val Asp Met Val Ser<br>            100                 105                 110 | | 336 |
| CTT GAA AAG TCA TTG CCG GAA GAG CTT GTT AAA GAG ATA ATT GAT AGA<br>Leu Glu Lys Ser Leu Pro Glu Glu Leu Val Lys Glu Ile Ile Asp Arg<br>        115                 120                 125 | | 384 |
| CGT AAA GAG CTT GGT TTG GAG GTA CCT AAA GTA AAG AAA CAT GTC TCG<br>Arg Lys Glu Leu Gly Leu Glu Val Pro Lys Val Lys Lys His Val Ser<br>130                 135                 140 | | 432 |
| AAT GTA CAT AAG GCA CTT GAC TCG GAT GAT ATT GAG TTA GTC AAG TTG<br>Asn Val His Lys Ala Leu Asp Ser Asp Asp Ile Glu Leu Val Lys Leu<br>145                 150                 155                 160 | | 480 |
| CTT TTG AAA GAG GAT CAC ACC AAT CTA GAT GAT GCG TGT GCT CTT CAT<br>Leu Leu Lys Glu Asp His Thr Asn Leu Asp Asp Ala Cys Ala Leu His<br>                165                 170                 175 | | 528 |

-continued

| | | |
|---|---|---|
| TTC GCT GTT GCA TAT TGC AAT GTG AAG ACC GCA ACA GAT CTT TTA AAA<br>Phe Ala Val Ala Tyr Cys Asn Val Lys Thr Ala Thr Asp Leu Leu Lys<br>                180                          185                        190 | 576 |
| CTT GAT CTT GCC GAT GTC AAC CAT AGG AAT CCG AGG GGA TAT ACG GTG<br>Leu Asp Leu Ala Asp Val Asn His Arg Asn Pro Arg Gly Tyr Thr Val<br>                195                          200                        205 | 624 |
| CTT CAT GTT GCT GCG ATG CGG AAG GAG CCA CAA TTG ATA CTA TCT CTA<br>Leu His Val Ala Ala Met Arg Lys Glu Pro Gln Leu Ile Leu Ser Leu<br>                210                          215                        220 | 672 |
| TTG GAA AAA GGT GCA AGT GCA TCA GAA GCA ACT TTG GAA GGT AGA ACC<br>Leu Glu Lys Gly Ala Ser Ala Ser Glu Ala Thr Leu Glu Gly Arg Thr<br>225                          230                        235                        240 | 720 |
| GCA CTC ATG ATC GCA AAA CAA GCC ACT ATG GCG GTT GAA TGT AAT AAT<br>Ala Leu Met Ile Ala Lys Gln Ala Thr Met Ala Val Glu Cys Asn Asn<br>                        245                        250                        255 | 768 |
| ATC CCG GAG CAA TGC AAG CAT TCT CTC AAA GGC CGA CTA TGT GTA GAA<br>Ile Pro Glu Gln Cys Lys His Ser Leu Lys Gly Arg Leu Cys Val Glu<br>                      260                        265                        270 | 816 |
| ATA CTA GAG CAA GAA GAC AAA CGA GAA CAA ATT CCT AGA GAT GTT CCT<br>Ile Leu Glu Gln Glu Asp Lys Arg Glu Gln Ile Pro Arg Asp Val Pro<br>                  275                        280                        285 | 864 |
| CCC TCT TTT GCA GTG GCG GCC GAT GAA TTG AAG ATG ACG CTG CTC GAT<br>Pro Ser Phe Ala Val Ala Ala Asp Glu Leu Lys Met Thr Leu Leu Asp<br>                290                          295                        300 | 912 |
| CTT GAA AAT AGA GTT GCA CTT GCT CAA CGT CTT TTT CCA ACG GAA GCA<br>Leu Glu Asn Arg Val Ala Leu Ala Gln Arg Leu Phe Pro Thr Glu Ala<br>305                          310                        315                        320 | 960 |
| CAA GCT GCA ATG GAG ATC GCC GAA ATG AAG GGA ACA TGT GAG TTC ATA<br>Gln Ala Ala Met Glu Ile Ala Glu Met Lys Gly Thr Cys Glu Phe Ile<br>                        325                        330                        335 | 1008 |
| GTG ACT AGC CTC GAG CCT GAC CGT CTC ACT GGT ACG AAG AGA ACA TCA<br>Val Thr Ser Leu Glu Pro Asp Arg Leu Thr Gly Thr Lys Arg Thr Ser<br>                340                          345                        350 | 1056 |
| CCG GGT GTA AAG ATA GCA CCT TTC AGA ATC CTA GAA GAG CAT CAA AGT<br>Pro Gly Val Lys Ile Ala Pro Phe Arg Ile Leu Glu Glu His Gln Ser<br>                    355                        360                        365 | 1104 |
| AGA CTA AAA GCG CTT TCT AAA ACC GTG GAA CTC GGG AAA CGA TTC TTC<br>Arg Leu Lys Ala Leu Ser Lys Thr Val Glu Leu Gly Lys Arg Phe Phe<br>            370                        375                        380 | 1152 |
| CCG CGC TGT TCG GCA GTG CTC GAC CAG ATT ATG AAC TGT GAG GAC TTG<br>Pro Arg Cys Ser Ala Val Leu Asp Gln Ile Met Asn Cys Glu Asp Leu<br>385                          390                        395                        400 | 1200 |
| ACT CAA CTG GCT TGC GGA GAA GAC GAC ACT GCT GAG AAA CGA CTA CAA<br>Thr Gln Leu Ala Cys Gly Glu Asp Asp Thr Ala Glu Lys Arg Leu Gln<br>                        405                        410                        415 | 1248 |
| AAG AAG CAA AGG TAC ATG GAA ATA CAA GAG ACA CTA AAG AAG GCC TTT<br>Lys Lys Gln Arg Tyr Met Glu Ile Gln Glu Thr Leu Lys Lys Ala Phe<br>                  420                          425                        430 | 1296 |
| AGT GAG GAC AAT TTG GAA TTA GGA AAT TTG TCC CTG ACA GAT TCG ACT<br>Ser Glu Asp Asn Leu Glu Leu Gly Asn Leu Ser Leu Thr Asp Ser Thr<br>              435                        440                        445 | 1344 |
| TCT TCC ACA TCG AAA TCA ACC GGT GGA AAG AGG TCT AAC CGT AAA CTC<br>Ser Ser Thr Ser Lys Ser Thr Gly Gly Lys Arg Ser Asn Arg Lys Leu<br>450                          455                        460 | 1392 |
| TCT CAT CGT CGT CGG TGA GACTCTTGCC TCTTAGTGTA ATTTTTGCTG<br>Ser His Arg Arg Arg  *<br>465                          470 | 1440 |
| TACCATATAA TTCTGTTTTC ATGATGACTG TAACTGTTTA TGTCTATCGT TGGCGTCATA | 1500 |
| TAGTTTCGCT CTTCGTTTTG CATCCTGTGT ATTATTGCTG CAGGTGTGCT TCAAACAAAT | 1560 |

-continued

```
GTTGTAACAA TTTGAACCAA TGGTATACAG ATTTGTA                                              1597
```

(2) INFORMATION FOR SEQ ID NO:10:

(i) SEQUENCE CHARACTERISTICS:
        (A) LENGTH: 469 amino acids
        (B) TYPE: amino acid
        (D) TOPOLOGY: linear (ii) MOLECULE TYPE: protein (xi) SEQUENCE DESCRIPTION: SEQ ID NO:10:

```
Met Asp Ser Val Val Thr Val Leu Ala Tyr Val Tyr Ser Ser Arg Val
  1               5                  10                  15

Arg Pro Pro Lys Gly Val Ser Glu Cys Ala Asp Glu Asn Cys Cys
                 20                  25                  30

His Val Ala Cys Arg Pro Ala Val Asp Phe Met Leu Glu Val Leu Tyr
             35                  40                  45

Leu Ala Phe Ile Phe Lys Ile Pro Glu Leu Ile Thr Leu Tyr Gln Arg
         50                  55                  60

His Leu Leu Asp Val Val Asp Lys Val Val Ile Glu Asp Thr Leu Val
 65                  70                  75                  80

Ile Leu Lys Leu Ala Asn Ile Cys Gly Lys Ala Cys Met Lys Leu Leu
                 85                  90                  95

Asp Arg Cys Lys Glu Ile Ile Val Lys Ser Asn Val Asp Met Val Ser
                100                 105                 110

Leu Glu Lys Ser Leu Pro Glu Glu Leu Val Lys Glu Ile Ile Asp Arg
            115                 120                 125

Arg Lys Glu Leu Gly Leu Glu Val Pro Lys Val Lys Lys His Val Ser
130                 135                 140

Asn Val His Lys Ala Leu Asp Ser Asp Ile Glu Leu Val Lys Leu
145                 150                 155                 160

Leu Leu Lys Glu Asp His Thr Asn Leu Asp Asp Ala Cys Ala Leu His
                165                 170                 175

Phe Ala Val Ala Tyr Cys Asn Val Lys Thr Ala Thr Asp Leu Leu Lys
            180                 185                 190

Leu Asp Leu Ala Asp Val Asn His Arg Asn Pro Arg Gly Tyr Thr Val
        195                 200                 205

Leu His Val Ala Ala Met Arg Lys Glu Pro Gln Leu Ile Leu Ser Leu
    210                 215                 220

Leu Glu Lys Gly Ala Ser Ala Ser Glu Ala Thr Leu Glu Gly Arg Thr
225                 230                 235                 240

Ala Leu Met Ile Ala Lys Gln Ala Thr Met Ala Val Glu Cys Asn Asn
                245                 250                 255

Ile Pro Glu Gln Cys Lys His Ser Leu Lys Gly Arg Leu Cys Val Glu
            260                 265                 270

Ile Leu Glu Gln Glu Asp Lys Arg Glu Gln Ile Pro Arg Asp Val Pro
        275                 280                 285

Pro Ser Phe Ala Val Ala Ala Asp Glu Leu Lys Met Thr Leu Leu Asp
    290                 295                 300

Leu Glu Asn Arg Val Ala Leu Ala Gln Arg Leu Phe Pro Thr Glu Ala
305                 310                 315                 320

Gln Ala Ala Met Glu Ile Ala Glu Met Lys Gly Thr Cys Glu Phe Ile
                325                 330                 335

Val Thr Ser Leu Glu Pro Asp Arg Leu Thr Gly Thr Lys Arg Thr Ser
            340                 345                 350
```

```
Pro Gly Val Lys Ile Ala Pro Phe Arg Ile Leu Glu Glu His Gln Ser
        355                 360                 365

Arg Leu Lys Ala Leu Ser Lys Thr Val Glu Leu Gly Lys Arg Phe Phe
    370                 375                 380

Pro Arg Cys Ser Ala Val Leu Asp Gln Ile Met Asn Cys Glu Asp Leu
385                 390                 395                 400

Thr Gln Leu Ala Cys Gly Glu Asp Thr Ala Glu Lys Arg Leu Gln
                405                 410                 415

Lys Lys Gln Arg Tyr Met Glu Ile Gln Glu Thr Leu Lys Lys Ala Phe
            420                 425                 430

Ser Glu Asp Asn Leu Glu Leu Gly Asn Leu Ser Leu Thr Asp Ser Thr
        435                 440                 445

Ser Ser Thr Ser Lys Ser Thr Gly Gly Lys Arg Ser Asn Arg Lys Leu
    450                 455                 460

Ser His Arg Arg Arg
465             470

(2) INFORMATION FOR SEQ ID NO:11:

(i) SEQUENCE CHARACTERISTICS:
        (A) LENGTH: 1608 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 43..1608
        (D) OTHER INFORMATION: /product= "Altered form of NIM1"
            /note= "C-terminal deletion compared to wild-type NIM1."

(xi) SEQUENCE DESCRIPTION: SEQ ID NO:11:

GATCTCTTTA ATTTGTGAAT TCAATTCAT CGGAACCTGT TG ATG GAC ACC ACC        54
                                              Met Asp Thr Thr
                                               1

ATT GAT GGA TTC GCC GAT TCT TAT GAA ATC AGC AGC ACT AGT TTC GTC    102
Ile Asp Gly Phe Ala Asp Ser Tyr Glu Ile Ser Ser Thr Ser Phe Val
 5                  10                  15                  20

GCT ACC GAT AAC ACC GAC TCC TCT ATT GTT TAT CTG GCC GCC GAA CAA    150
Ala Thr Asp Asn Thr Asp Ser Ser Ile Val Tyr Leu Ala Ala Glu Gln
                25                  30                  35

GTA CTC ACC GGA CCT GAT GTA TCT GCT CTG CAA TTG CTC TCC AAC AGC    198
Val Leu Thr Gly Pro Asp Val Ser Ala Leu Gln Leu Leu Ser Asn Ser
            40                  45                  50

TTC GAA TCC GTC TTT GAC TCG CCG GAT GAT TTC TAC AGC GAC GCT AAG    246
Phe Glu Ser Val Phe Asp Ser Pro Asp Asp Phe Tyr Ser Asp Ala Lys
        55                  60                  65

CTT GTT CTC TCC GAC GGC CGG GAA GTT TCT TTC CAC CGG TGC GTT TTG    294
Leu Val Leu Ser Asp Gly Arg Glu Val Ser Phe His Arg Cys Val Leu
    70                  75                  80

TCA GCG AGA AGC TCT TTC TTC AAG AGC GCT TTA GCC GCC GCT AAG AAG    342
Ser Ala Arg Ser Ser Phe Phe Lys Ser Ala Leu Ala Ala Ala Lys Lys
85                  90                  95                 100

GAG AAA GAC TCC AAC AAC ACC GCC GCC GTG AAG CTC GAG CTT AAG GAG    390
Glu Lys Asp Ser Asn Asn Thr Ala Ala Val Lys Leu Glu Leu Lys Glu
                105                 110                 115

ATT GCC AAG GAT TAC GAA GTC GGT TTC GAT TCG GTT GTG ACT GTT TTG    438
Ile Ala Lys Asp Tyr Glu Val Gly Phe Asp Ser Val Val Thr Val Leu
            120                 125                 130
```

```
GCT TAT GTT TAC AGC AGC AGA GTG AGA CCG CCG CCT AAA GGA GTT TCT        486
Ala Tyr Val Tyr Ser Ser Arg Val Arg Pro Pro Pro Lys Gly Val Ser
            135                 140                 145

GAA TGC GCA GAC GAG AAT TGC TGC CAC GTG GCT TGC CGG CCG GCG GTG        534
Glu Cys Ala Asp Glu Asn Cys Cys His Val Ala Cys Arg Pro Ala Val
150                 155                 160

GAT TTC ATG TTG GAG GTT CTC TAT TTG GCT TTC ATC TTC AAG ATC CCT        582
Asp Phe Met Leu Glu Val Leu Tyr Leu Ala Phe Ile Phe Lys Ile Pro
165                 170                 175                 180

GAA TTA ATT ACT CTC TAT CAG AGG CAC TTA TTG GAC GTT GTA GAC AAA        630
Glu Leu Ile Thr Leu Tyr Gln Arg His Leu Leu Asp Val Val Asp Lys
            185                 190                 195

GTT GTT ATA GAG GAC ACA TTG GTT ATA CTC AAG CTT GCT AAT ATA TGT        678
Val Val Ile Glu Asp Thr Leu Val Ile Leu Lys Leu Ala Asn Ile Cys
            200                 205                 210

GGT AAA GCT TGT ATG AAG CTA TTG GAT AGA TGT AAA GAG ATT ATT GTC        726
Gly Lys Ala Cys Met Lys Leu Leu Asp Arg Cys Lys Glu Ile Ile Val
            215                 220                 225

AAG TCT AAT GTA GAT ATG GTT AGT CTT GAA AAG TCA TTG CCG GAA GAG        774
Lys Ser Asn Val Asp Met Val Ser Leu Glu Lys Ser Leu Pro Glu Glu
            230                 235                 240

CTT GTT AAA GAG ATA ATT GAT AGA CGT AAA GAG CTT GGT TTG GAG GTA        822
Leu Val Lys Glu Ile Ile Asp Arg Arg Lys Glu Leu Gly Leu Glu Val
245                 250                 255                 260

CCT AAA GTA AAG AAA CAT GTC TCG AAT GTA CAT AAG GCA CTT GAC TCG        870
Pro Lys Val Lys Lys His Val Ser Asn Val His Lys Ala Leu Asp Ser
            265                 270                 275

GAT GAT ATT GAG TTA GTC AAG TTG CTT TTG AAA GAG GAT CAC ACC AAT        918
Asp Asp Ile Glu Leu Val Lys Leu Leu Leu Lys Glu Asp His Thr Asn
            280                 285                 290

CTA GAT GAT GCG TGT GCT CTT CAT TTC GCT GTT GCA TAT TGC AAT GTG        966
Leu Asp Asp Ala Cys Ala Leu His Phe Ala Val Ala Tyr Cys Asn Val
            295                 300                 305

AAG ACC GCA ACA GAT CTT TTA AAA CTT GAT CTT GCC GAT GTC AAC CAT       1014
Lys Thr Ala Thr Asp Leu Leu Lys Leu Asp Leu Ala Asp Val Asn His
310                 315                 320

AGG AAT CCG AGG GGA TAT ACG GTG CTT CAT GTT GCT GCG ATG CGG AAG       1062
Arg Asn Pro Arg Gly Tyr Thr Val Leu His Val Ala Ala Met Arg Lys
325                 330                 335                 340

GAG CCA CAA TTG ATA CTA TCT CTA TTG GAA AAA GGT GCA AGT GCA TCA       1110
Glu Pro Gln Leu Ile Leu Ser Leu Leu Glu Lys Gly Ala Ser Ala Ser
            345                 350                 355

GAA GCA ACT TTG GAA GGT AGA ACC GCA CTC ATG ATC GCA AAA CAA GCC       1158
Glu Ala Thr Leu Glu Gly Arg Thr Ala Leu Met Ile Ala Lys Gln Ala
            360                 365                 370

ACT ATG GCG GTT GAA TGT AAT AAT ATC CCG GAG CAA TGC AAG CAT TCT       1206
Thr Met Ala Val Glu Cys Asn Asn Ile Pro Glu Gln Cys Lys His Ser
            375                 380                 385

CTC AAA GGC CGA CTA TGT GTA GAA ATA CTA GAG CAA GAA GAC AAA CGA       1254
Leu Lys Gly Arg Leu Cys Val Glu Ile Leu Glu Gln Glu Asp Lys Arg
390                 395                 400

GAA CAA ATT CCT AGA GAT GTT CCT CCC TCT TTT GCA GTG GCG GCC GAT       1302
Glu Gln Ile Pro Arg Asp Val Pro Pro Ser Phe Ala Val Ala Ala Asp
405                 410                 415                 420

GAA TTG AAG ATG ACG CTG CTC GAT CTT GAA AAT AGA GTT GCA CTT GCT       1350
Glu Leu Lys Met Thr Leu Leu Asp Leu Glu Asn Arg Val Ala Leu Ala
            425                 430                 435

CAA CGT CTT TTT CCA ACG GAA GCA CAA GCT GCA ATG GAG ATC GCC GAA       1398
Gln Arg Leu Phe Pro Thr Glu Ala Gln Ala Ala Met Glu Ile Ala Glu
            440                 445                 450
```

```
ATG AAG GGA ACA TGT GAG TTC ATA GTG ACT AGC CTC GAG CCT GAC CGT      1446
Met Lys Gly Thr Cys Glu Phe Ile Val Thr Ser Leu Glu Pro Asp Arg
        455                 460                 465

CTC ACT GGT ACG AAG AGA ACA TCA CCG GGT GTA AAG ATA GCA CCT TTC      1494
Leu Thr Gly Thr Lys Arg Thr Ser Pro Gly Val Lys Ile Ala Pro Phe
    470                 475                 480

AGA ATC CTA GAA GAG CAT CAA AGT AGA CTA AAA GCG CTT TCT AAA ACC      1542
Arg Ile Leu Glu Glu His Gln Ser Arg Leu Lys Ala Leu Ser Lys Thr
485                 490                 495                 500

GTG GAA CTC GGG AAA CGA TTC TTC CCG CGC TGT TCG GCA GTG CTC GAC      1590
Val Glu Leu Gly Lys Arg Phe Phe Pro Arg Cys Ser Ala Val Leu Asp
            505                 510                 515

CAG ATT ATG AAC TGT TGA                                              1608
Gln Ile Met Asn Cys *
        520
```

(2) INFORMATION FOR SEQ ID NO:12:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asp Thr Thr Ile Asp Gly Phe Ala Asp Ser Tyr Glu Ile Ser Ser
 1               5                  10                  15

Thr Ser Phe Val Ala Thr Asp Asn Thr Asp Ser Ser Ile Val Tyr Leu
                20                  25                  30

Ala Ala Glu Gln Val Leu Thr Gly Pro Asp Val Ser Ala Leu Gln Leu
            35                  40                  45

Leu Ser Asn Ser Phe Glu Ser Val Phe Asp Ser Pro Asp Asp Phe Tyr
    50                  55                  60

Ser Asp Ala Lys Leu Val Leu Ser Asp Gly Arg Glu Val Ser Phe His
65                  70                  75                  80

Arg Cys Val Leu Ser Ala Arg Ser Ser Phe Phe Lys Ser Ala Leu Ala
                85                  90                  95

Ala Ala Lys Lys Glu Lys Asp Ser Asn Asn Thr Ala Ala Val Lys Leu
            100                 105                 110

Glu Leu Lys Glu Ile Ala Lys Asp Tyr Glu Val Gly Phe Asp Ser Val
    115                 120                 125

Val Thr Val Leu Ala Tyr Val Tyr Ser Ser Arg Val Arg Pro Pro Pro
130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
            180                 185                 190

Val Val Asp Lys Val Val Ile Glu Asp Thr Leu Val Ile Leu Lys Leu
    195                 200                 205

Ala Asn Ile Cys Gly Lys Ala Cys Met Lys Leu Leu Asp Arg Cys Lys
210                 215                 220

Glu Ile Ile Val Lys Ser Asn Val Asp Met Val Ser Leu Glu Lys Ser
225                 230                 235                 240

Leu Pro Glu Glu Leu Val Lys Glu Ile Ile Asp Arg Arg Lys Glu Leu
                245                 250                 255
```

```
Gly Leu Glu Val Pro Lys Val Lys Lys His Val Ser Asn Val His Lys
                260                 265                 270
Ala Leu Asp Ser Asp Ile Glu Leu Val Lys Leu Leu Leu Lys Glu
            275                 280                 285
Asp His Thr Asn Leu Asp Ala Cys Ala Leu His Phe Ala Val Ala
        290                 295                 300
Tyr Cys Asn Val Lys Thr Ala Thr Asp Leu Leu Lys Leu Asp Leu Ala
305                 310                 315                 320
Asp Val Asn His Arg Asn Pro Arg Gly Tyr Thr Val Leu His Val Ala
                325                 330                 335
Ala Met Arg Lys Glu Pro Gln Leu Ile Leu Ser Leu Leu Glu Lys Gly
                340                 345                 350
Ala Ser Ala Ser Glu Ala Thr Leu Glu Gly Arg Thr Ala Leu Met Ile
                355                 360                 365
Ala Lys Gln Ala Thr Met Ala Val Glu Cys Asn Asn Ile Pro Glu Gln
            370                 375                 380
Cys Lys His Ser Leu Lys Gly Arg Leu Cys Val Glu Ile Leu Glu Gln
385                 390                 395                 400
Glu Asp Lys Arg Glu Gln Ile Pro Arg Asp Val Pro Pro Ser Phe Ala
                405                 410                 415
Val Ala Ala Asp Glu Leu Lys Met Thr Leu Leu Asp Leu Glu Asn Arg
                420                 425                 430
Val Ala Leu Ala Gln Arg Leu Phe Pro Thr Glu Ala Gln Ala Ala Met
            435                 440                 445
Glu Ile Ala Glu Met Lys Gly Thr Cys Glu Phe Ile Val Thr Ser Leu
450                 455                 460
Glu Pro Asp Arg Leu Thr Gly Thr Lys Arg Thr Ser Pro Gly Val Lys
465                 470                 475                 480
Ile Ala Pro Phe Arg Ile Leu Glu Glu His Gln Ser Arg Leu Lys Ala
                485                 490                 495
Leu Ser Lys Thr Val Glu Leu Gly Lys Arg Phe Phe Pro Arg Cys Ser
                500                 505                 510
Ala Val Leu Asp Gln Ile Met Asn Cys
            515                 520

(2) INFORMATION FOR SEQ ID NO:13:

(i) SEQUENCE CHARACTERISTICS:
        (A) LENGTH: 1194 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1194
        (D) OTHER INFORMATION: /product= "Altered form of NIM1"
            /note= "N-terminal/C-terminal chimera."

(xi) SEQUENCE DESCRIPTION: SEQ ID NO:13:

ATG GAT TCG GTT GTG ACT GTT TTG GCT TAT GTT TAC AGC AGC AGA GTG      48
Met Asp Ser Val Val Thr Val Leu Ala Tyr Val Tyr Ser Ser Arg Val
 1               5                  10                  15

AGA CCG CCG CCT AAA GGA GTT TCT GAA TGC GCA GAC GAG AAT TGC TGC      96
Arg Pro Pro Pro Lys Gly Val Ser Glu Cys Ala Asp Glu Asn Cys Cys
             20                  25                  30
```

| | | |
|---|---|---|
| CAC GTG GCT TGC CGG CCG GCG GTG GAT TTC ATG TTG GAG GTT CTC TAT<br>His Val Ala Cys Arg Pro Ala Val Asp Phe Met Leu Glu Val Leu Tyr<br>35                     40                       45 | 144 |
| TTG GCT TTC ATC TTC AAG ATC CCT GAA TTA ATT ACT CTC TAT CAG AGG<br>Leu Ala Phe Ile Phe Lys Ile Pro Glu Leu Ile Thr Leu Tyr Gln Arg<br>50                     55                       60 | 192 |
| CAC TTA TTG GAC GTT GTA GAC AAA GTT GTT ATA GAG GAC ACA TTG GTT<br>His Leu Leu Asp Val Val Asp Lys Val Val Ile Glu Asp Thr Leu Val<br>65                     70                     75                     80 | 240 |
| ATA CTC AAG CTT GCT AAT ATA TGT GGT AAA GCT TGT ATG AAG CTA TTG<br>Ile Leu Lys Leu Ala Asn Ile Cys Gly Lys Ala Cys Met Lys Leu Leu<br>                   85                     90                     95 | 288 |
| GAT AGA TGT AAA GAG ATT ATT GTC AAG TCT AAT GTA GAT ATG GTT AGT<br>Asp Arg Cys Lys Glu Ile Ile Val Lys Ser Asn Val Asp Met Val Ser<br>             100                      105                    110 | 336 |
| CTT GAA AAG TCA TTG CCG GAA GAG CTT GTT AAA GAG ATA ATT GAT AGA<br>Leu Glu Lys Ser Leu Pro Glu Glu Leu Val Lys Glu Ile Ile Asp Arg<br>             115                      120                    125 | 384 |
| CGT AAA GAG CTT GGT TTG GAG GTA CCT AAA GTA AAG AAA CAT GTC TCG<br>Arg Lys Glu Leu Gly Leu Glu Val Pro Lys Val Lys Lys His Val Ser<br>       130                      135                    140 | 432 |
| AAT GTA CAT AAG GCA CTT GAC TCG GAT GAT ATT GAG TTA GTC AAG TTG<br>Asn Val His Lys Ala Leu Asp Ser Asp Asp Ile Glu Leu Val Lys Leu<br>145                     150                     155                    160 | 480 |
| CTT TTG AAA GAG GAT CAC ACC AAT CTA GAT GAT GCG TGT GCT CTT CAT<br>Leu Leu Lys Glu Asp His Thr Asn Leu Asp Asp Ala Cys Ala Leu His<br>                   165                      170                    175 | 528 |
| TTC GCT GTT GCA TAT TGC AAT GTG AAG ACC GCA ACA GAT CTT TTA AAA<br>Phe Ala Val Ala Tyr Cys Asn Val Lys Thr Ala Thr Asp Leu Leu Lys<br>             180                      185                    190 | 576 |
| CTT GAT CTT GCC GAT GTC AAC CAT AGG AAT CCG AGG GGA TAT ACG GTG<br>Leu Asp Leu Ala Asp Val Asn His Arg Asn Pro Arg Gly Tyr Thr Val<br>       195                      200                    205 | 624 |
| CTT CAT GTT GCT GCG ATG CGG AAG GAG CCA CAA TTG ATA CTA TCT CTA<br>Leu His Val Ala Ala Met Arg Lys Glu Pro Gln Leu Ile Leu Ser Leu<br>210                     215                     220 | 672 |
| TTG GAA AAA GGT GCA AGT GCA TCA GAA GCA ACT TTG GAA GGT AGA ACC<br>Leu Glu Lys Gly Ala Ser Ala Ser Glu Ala Thr Leu Glu Gly Arg Thr<br>225                     230                     235                    240 | 720 |
| GCA CTC ATG ATC GCA AAA CAA GCC ACT ATG GCG GTT GAA TGT AAT AAT<br>Ala Leu Met Ile Ala Lys Gln Ala Thr Met Ala Val Glu Cys Asn Asn<br>                   245                      250                    255 | 768 |
| ATC CCG GAG CAA TGC AAG CAT TCT CTC AAA GGC CGA CTA TGT GTA GAA<br>Ile Pro Glu Gln Cys Lys His Ser Leu Lys Gly Arg Leu Cys Val Glu<br>             260                      265                    270 | 816 |
| ATA CTA GAG CAA GAA GAC AAA CGA GAA CAA ATT CCT AGA GAT GTT CCT<br>Ile Leu Glu Gln Glu Asp Lys Arg Glu Gln Ile Pro Arg Asp Val Pro<br>       275                      280                    285 | 864 |
| CCC TCT TTT GCA GTG GCG GCC GAT GAA TTG AAG ATG ACG CTG CTC GAT<br>Pro Ser Phe Ala Val Ala Ala Asp Glu Leu Lys Met Thr Leu Leu Asp<br>       290                      295                    300 | 912 |
| CTT GAA AAT AGA GTT GCA CTT GCT CAA CGT CTT TTT CCA ACG GAA GCA<br>Leu Glu Asn Arg Val Ala Leu Ala Gln Arg Leu Phe Pro Thr Glu Ala<br>305                     310                     315                    320 | 960 |
| CAA GCT GCA ATG GAG ATC GCC GAA ATG AAG GGA ACA TGT GAG TTC ATA<br>Gln Ala Ala Met Glu Ile Ala Glu Met Lys Gly Thr Cys Glu Phe Ile<br>                   325                      330                    335 | 1008 |
| GTG ACT AGC CTC GAG CCT GAC CGT CTC ACT GGT ACG AAG AGA ACA TCA<br>Val Thr Ser Leu Glu Pro Asp Arg Leu Thr Gly Thr Lys Arg Thr Ser<br>             340                      345                    350 | 1056 |

| | | | | | | | | | | | | |
|---|---|---|---|---|---|---|---|---|---|---|---|---|
| CCG | GGT | GTA | AAG | ATA | GCA | CCT | TTC | AGA | ATC | CTA | GAA | GAG | CAT | CAA | AGT | 1104 |
| Pro | Gly | Val | Lys | Ile | Ala | Pro | Phe | Arg | Ile | Leu | Glu | Glu | His | Gln | Ser | |
| | | 355 | | | | 360 | | | | | 365 | | | | | |

```
CCG GGT GTA AAG ATA GCA CCT TTC AGA ATC CTA GAA GAG CAT CAA AGT     1104
Pro Gly Val Lys Ile Ala Pro Phe Arg Ile Leu Glu Glu His Gln Ser
        355             360                 365

AGA CTA AAA GCG CTT TCT AAA ACC GTG AAA CTC GGG AAA CGA TTC TTC     1152
Arg Leu Lys Ala Leu Ser Lys Thr Val Glu Leu Gly Lys Arg Phe Phe
370             375                 380

CCG CGC TGT TCG GCA GTG CTC GAC CAG ATT ATG AAC TGT TGA             1194
Pro Arg Cys Ser Ala Val Leu Asp Gln Ile Met Asn Cys *
385             390                 395
```

(2) INFORMATION FOR SEQ ID NO:14:

(i) SEQUENCE CHARACTERISTICS:
      (A) LENGTH: 397 amino acids
      (B) TYPE: amino acid
      (D) TOPOLOGY: linear (ii) MOLECULE TYPE: protein (xi) SEQUENCE DESCRIPTION: SEQ ID NO:14:

```
Met Asp Ser Val Val Thr Val Leu Ala Tyr Val Tyr Ser Ser Arg Val
 1               5                  10                  15

Arg Pro Pro Lys Gly Val Ser Glu Cys Ala Asp Glu Asn Cys Cys
            20                  25                  30

His Val Ala Cys Arg Pro Ala Val Asp Phe Met Leu Glu Val Leu Tyr
         35                  40                  45

Leu Ala Phe Ile Phe Lys Ile Pro Glu Leu Ile Thr Leu Tyr Gln Arg
     50                  55                  60

His Leu Leu Asp Val Val Asp Lys Val Val Ile Glu Asp Thr Leu Val
 65                  70                  75                  80

Ile Leu Lys Leu Ala Asn Ile Cys Gly Lys Ala Cys Met Lys Leu Leu
                 85                  90                  95

Asp Arg Cys Lys Glu Ile Ile Val Lys Ser Asn Val Asp Met Val Ser
             100                 105                 110

Leu Glu Lys Ser Leu Pro Glu Glu Leu Val Lys Glu Ile Ile Asp Arg
         115                 120                 125

Arg Lys Glu Leu Gly Leu Glu Val Pro Lys Val Lys Lys His Val Ser
    130                 135                 140

Asn Val His Lys Ala Leu Asp Ser Asp Ile Glu Leu Val Lys Leu
145                 150                 155                 160

Leu Leu Lys Glu Asp His Thr Asn Leu Asp Asp Ala Cys Ala Leu His
                 165                 170                 175

Phe Ala Val Ala Tyr Cys Asn Val Lys Thr Ala Thr Asp Leu Leu Lys
             180                 185                 190

Leu Asp Leu Ala Asp Val Asn His Arg Asn Pro Arg Gly Tyr Thr Val
         195                 200                 205

Leu His Val Ala Ala Met Arg Lys Glu Pro Gln Leu Ile Leu Ser Leu
    210                 215                 220

Leu Glu Lys Gly Ala Ser Ala Ser Glu Ala Thr Leu Glu Gly Arg Thr
225                 230                 235                 240

Ala Leu Met Ile Ala Lys Gln Ala Thr Met Ala Val Glu Cys Asn Asn
                 245                 250                 255

Ile Pro Glu Gln Cys Lys His Ser Leu Lys Gly Arg Leu Cys Val Glu
             260                 265                 270

Ile Leu Glu Gln Glu Asp Lys Arg Glu Gln Ile Pro Arg Asp Val Pro
         275                 280                 285

Pro Ser Phe Ala Val Ala Ala Asp Glu Leu Lys Met Thr Leu Leu Asp
    290                 295                 300
```

```
Leu Glu Asn Arg Val Ala Leu Ala Gln Arg Leu Phe Pro Thr Glu Ala
305                 310                 315                 320

Gln Ala Ala Met Glu Ile Ala Glu Met Lys Gly Thr Cys Glu Phe Ile
            325                 330                 335

Val Thr Ser Leu Glu Pro Asp Arg Leu Thr Gly Thr Lys Arg Thr Ser
            340                 345                 350

Pro Gly Val Lys Ile Ala Pro Phe Arg Ile Leu Glu His Gln Ser
            355                 360                 365

Arg Leu Lys Ala Leu Ser Lys Thr Val Glu Leu Gly Lys Arg Phe Phe
        370                 375                 380

Pro Arg Cys Ser Ala Val Leu Asp Gln Ile Met Asn Cys
385                 390                 395
```

(2) INFORMATION FOR SEQ ID NO:15:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..786
        (D) OTHER INFORMATION: /product= "Altered form of NIM1"
            /note= "Ankyrin domains of NIM1."

(xi) SEQUENCE DESCRIPTION: SEQ ID NO:15:

```
ATG GAC TCC AAC AAC ACC GCC GCC GTG AAG CTC GAG CTT AAG GAG ATT     48
Met Asp Ser Asn Asn Thr Ala Ala Val Lys Leu Glu Leu Lys Glu Ile
 1               5                  10                  15

GCC AAG GAT TAC GAA GTC GGT TTC GAT TCG GTT GTG ACT GTT TTG GCT     96
Ala Lys Asp Tyr Glu Val Gly Phe Asp Ser Val Val Thr Val Leu Ala
                20                  25                  30

TAT GTT TAC AGC AGC AGA GTG AGA CCG CCG CCT AAA GGA GTT TCT GAA    144
Tyr Val Tyr Ser Ser Arg Val Arg Pro Pro Pro Lys Gly Val Ser Glu
            35                  40                  45

TGC GCA GAC GAG AAT TGC TGC CAC GTG GCT TGC CGG CCG GCG GTG GAT    192
Cys Ala Asp Glu Asn Cys Cys His Val Ala Cys Arg Pro Ala Val Asp
    50                  55                  60

TTC ATG TTG GAG GTT CTC TAT TTG GCT TTC ATC TTC AAG ATC CCT GAA    240
Phe Met Leu Glu Val Leu Tyr Leu Ala Phe Ile Phe Lys Ile Pro Glu
65                  70                  75                  80

TTA ATT ACT CTC TAT CAG AGG CAC TTA TTG GAC GTT GTA GAC AAA GTT    288
Leu Ile Thr Leu Tyr Gln Arg His Leu Leu Asp Val Val Asp Lys Val
                85                  90                  95

GTT ATA GAG GAC ACA TTG GTT ATA CTC AAG CTT GCT AAT ATA TGT GGT    336
Val Ile Glu Asp Thr Leu Val Ile Leu Lys Leu Ala Asn Ile Cys Gly
            100                 105                 110

AAA GCT TGT ATG AAG CTA TTG GAT AGA TGT AAA GAG ATT ATT GTC AAG    384
Lys Ala Cys Met Lys Leu Leu Asp Arg Cys Lys Glu Ile Ile Val Lys
        115                 120                 125

TCT AAT GTA GAT ATG GTT AGT CTT GAA AAG TCA TTG CCG GAA GAG CTT    432
Ser Asn Val Asp Met Val Ser Leu Glu Lys Ser Leu Pro Glu Glu Leu
    130                 135                 140

GTT AAA GAG ATA ATT GAT AGA CGT AAA GAG CTT GGT TTG GAG GTA CCT    480
Val Lys Glu Ile Ile Asp Arg Arg Lys Glu Leu Gly Leu Glu Val Pro
145                 150                 155                 160
```

```
AAA GTA AAG AAA CAT GTC TCG AAT GTA CAT AAG GCA CTT GAC TCG GAT         528
Lys Val Lys Lys His Val Ser Asn Val His Lys Ala Leu Asp Ser Asp
            165                 170                 175

GAT ATT GAG TTA GTC AAG TTG CTT TTG AAA GAG GAT CAC ACC AAT CTA         576
Asp Ile Glu Leu Val Lys Leu Leu Leu Lys Glu Asp His Thr Asn Leu
        180                 185                 190

GAT GAT GCG TGT GCT CTT CAT TTC GCT GTT GCA TAT TGC AAT GTG AAG         624
Asp Asp Ala Cys Ala Leu His Phe Ala Val Ala Tyr Cys Asn Val Lys
    195                 200                 205

ACC GCA ACA GAT CTT TTA AAA CTT GAT CTT GCC GAT GTC AAC CAT AGG         672
Thr Ala Thr Asp Leu Leu Lys Leu Asp Leu Ala Asp Val Asn His Arg
210                 215                 220

AAT CCG AGG GGA TAT ACG GTG CTT CAT GTT GCT GCG ATG CGG AAG GAG         720
Asn Pro Arg Gly Tyr Thr Val Leu His Val Ala Ala Met Arg Lys Glu
225                 230                 235                 240

CCA CAA TTG ATA CTA TCT CTA TTG GAA AAA GGT GCA AGT GCA TCA GAA         768
Pro Gln Leu Ile Leu Ser Leu Leu Glu Lys Gly Ala Ser Ala Ser Glu
                245                 250                 255

GCA ACT TTG GAA GGT TGA                                                  786
Ala Thr Leu Glu Gly *
260
```

(2) INFORMATION FOR SEQ ID NO:16:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:16:

```
Met Asp Ser Asn Asn Thr Ala Ala Val Lys Leu Glu Leu Lys Glu Ile
1               5                   10                  15

Ala Lys Asp Tyr Glu Val Gly Phe Asp Ser Val Thr Val Leu Ala
            20                  25                  30

Tyr Val Tyr Ser Ser Arg Val Arg Pro Pro Lys Gly Val Ser Glu
        35                  40                  45

Cys Ala Asp Glu Asn Cys Cys His Val Ala Cys Arg Pro Ala Val Asp
    50                  55                  60

Phe Met Leu Glu Val Leu Tyr Leu Ala Phe Ile Phe Lys Ile Pro Glu
65                  70                  75                  80

Leu Ile Thr Leu Tyr Gln Arg His Leu Leu Asp Val Val Asp Lys Val
                85                  90                  95

Val Ile Glu Asp Thr Leu Val Ile Leu Lys Leu Ala Asn Ile Cys Gly
            100                 105                 110

Lys Ala Cys Met Lys Leu Leu Asp Arg Cys Lys Glu Ile Ile Val Lys
        115                 120                 125

Ser Asn Val Asp Met Val Ser Leu Glu Lys Ser Leu Pro Glu Glu Leu
    130                 135                 140

Val Lys Glu Ile Ile Asp Arg Arg Lys Glu Leu Gly Leu Glu Val Pro
145                 150                 155                 160

Lys Val Lys Lys His Val Ser Asn Val His Lys Ala Leu Asp Ser Asp
                165                 170                 175

Asp Ile Glu Leu Val Lys Leu Leu Leu Lys Glu Asp His Thr Asn Leu
            180                 185                 190

Asp Asp Ala Cys Ala Leu His Phe Ala Val Ala Tyr Cys Asn Val Lys
        195                 200                 205
```

```
Thr Ala Thr Asp Leu Leu Lys Leu Asp Leu Ala Asp Val Asn His Arg
    210                 215                 220

Asn Pro Arg Gly Tyr Thr Val Leu His Val Ala Ala Met Arg Lys Glu
225                 230                 235                 240

Pro Gln Leu Ile Leu Ser Leu Leu Glu Lys Gly Ala Ser Ala Ser Glu
                245                 250                 255

Ala Thr Leu Glu Gly
        260
```

(2) INFORMATION FOR SEQ ID NO:17:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:17:

```
Ile Arg Arg Met Arg Arg Ala Leu Asp Ala Ala Asp Ile Glu Leu Val
1               5                   10                  15

Lys Leu Met Val Met Gly Glu Gly Leu Asp Leu Asp Asp Ala Leu Ala
                20                  25                  30

Val His Tyr Ala Val Gln His Cys Asn
            35                  40
```

(2) INFORMATION FOR SEQ ID NO:18:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:18:

```
Pro Thr Gly Lys Thr Ala Leu His Leu Ala Ala Glu Met Val Ser Pro
1               5                   10                  15

Asp Met Val Ser Val Leu Leu Asp His His Ala Asp Xaa Asn Phe Arg
                20                  25                  30

Thr Xaa Asp Gly Val Thr
        35
```

(2) INFORMATION FOR SEQ ID NO:19:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:19:

```
Ile Arg Arg Met Arg Arg Ala Leu Asp Ala Ala Asp Ile Glu Leu Val
1               5                   10                  15

Lys Leu Met Val Met Gly Glu Gly Leu Asp Leu Asp Asp Ala Leu Ala
                20                  25                  30

Val His Tyr Ala Val Gln His Cys Asn
            35                  40
```

(2) INFORMATION FOR SEQ ID NO:20:

(i) SEQUENCE CHARACTERISTICS:
            (A) LENGTH: 27 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:20:

Arg Arg Pro Asp Ser Lys Thr Ala Leu His Leu Ala Ala Glu Met Val
    1               5                   10                  15

Ser Pro Asp Met Val Ser Val Leu Leu Asp Gln
                20                  25

(2) INFORMATION FOR SEQ ID NO:21:

(i) SEQUENCE CHARACTERISTICS:
            (A) LENGTH: 41 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:21:

Ile Arg Arg Met Arg Arg Ala Leu Asp Ala Ala Asp Ile Glu Leu Val
    1               5                   10                  15

Lys Leu Met Val Met Gly Glu Gly Leu Asp Leu Asp Asp Ala Leu Ala
                20                  25                  30

Val His Tyr Ala Val Gln His Cys Asn
                35                  40

(2) INFORMATION FOR SEQ ID NO:22:

(i) SEQUENCE CHARACTERISTICS:
            (A) LENGTH: 27 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:22:

Arg Arg Pro Asp Ser Lys Thr Ala Leu His Leu Ala Ala Glu Met Val
    1               5                   10                  15

Ser Pro Asp Met Val Ser Val Leu Leu Asp Gln
                20                  25

(2) INFORMATION FOR SEQ ID NO:23:

(i) SEQUENCE CHARACTERISTICS:
            (A) LENGTH: 41 amino acids
            (B) TYPE: amino acid
            (C) STRANDEDNESS: Not Relevant
            (D) TOPOLOGY: Not Relevant (ii) MOLECULE TYPE: peptide (xi) SEQUENCE DESCRIPTION: SEQ ID NO:23:

Ile Arg Arg Met Arg Arg Ala Leu Asp Ala Ala Asp Ile Glu Leu Val
    1               5                   10                  15

Lys Leu Met Val Met Gly Glu Gly Leu Asp Leu Asp Asp Ala Leu Ala
                20                  25                  30

Val His Tyr Ala Val Gln His Cys Asn
                35                  40

(2) INFORMATION FOR SEQ ID NO:24:

(i) SEQUENCE CHARACTERISTICS:
      (A) LENGTH: 19 amino acids
      (B) TYPE: amino acid
      (C) STRANDEDNESS: Not Relevant
      (D) TOPOLOGY: Not Relevant (ii) MOLECULE TYPE: peptide (xi) SEQUENCE DESCRIPTION: SEQ ID NO:24:

Pro Thr Gly Lys Thr Ala Leu His Leu Ala Ala Glu Met Val Ser Pro
   1               5                  10                  15

Asp Met Val (2) INFORMATION FOR SEQ ID NO:25:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:25:

CAACAGCTTC GAAGCCGTCT TTGACGCGCC GGATG                      35

(2) INFORMATION FOR SEQ ID NO:26:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:26:

CATCCGGCGC GTCAAAGACG GCTTCGAAGC TGTTG                      35

(2) INFORMATION FOR SEQ ID NO:27:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "oligonucleotide"

(xi) SEQUENCE DESCRIPTION: SEQ ID NO:27:

GGAATTCAAT GGATTCGGTT GTGACTGTTT TG                         32

(2) INFORMATION FOR SEQ ID NO:28:

(i) SEQUENCE CHARACTERISTICS:
      (A) LENGTH: 28 base pairs
      (B) TYPE: nucleic acid
      (C) STRANDEDNESS: single
      (D) TOPOLOGY: linear -continued

```
    (ii) MOLECULE TYPE: other nucleic acid
         (A) DESCRIPTION: /desc = "oligonucleotide"

(xi) SEQUENCE DESCRIPTION: SEQ ID NO:28:

GGAATTCTAC AAATCTGTAT ACCATTGG                                          28

(2) INFORMATION FOR SEQ ID NO:29:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO:29:

CGGAATTCGA TCTCTTTAAT TTGTGAATTT C                                      31

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO:30:

GGAATTCTCA ACAGTTCATA ATCTGGTCG                                         29

(2) INFORMATION FOR SEQ ID NO:31:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO:31:

GGAATTCAAT GGACTCCAAC AACACCGCCG C                                      31

(2) INFORMATION FOR SEQ ID NO:32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "oligonucleotide"

(xi) SEQUENCE DESCRIPTION: SEQ ID NO:32:

GGAATTCTCA ACCTTCCAAA GTTGCTTCTG ATG                                    33
```